United States Patent
Kesari et al.

(10) Patent No.: US 10,258,629 B2
(45) Date of Patent: Apr. 16, 2019

(54) LIPOSOMAL DRUG ENCAPSULATION

(71) Applicant: The Regents of the University of California, Oakland, CA (US)

(72) Inventors: Santosh Kesari, San Diego, CA (US); Rajesh Mukthavaram, La Jolla, CA (US); Milan T. Makale, San Diego, CA (US); Wolfgang J. Wrasidlo, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/129,317

(22) PCT Filed: Mar. 27, 2015

(86) PCT No.: PCT/US2015/023109
§ 371 (c)(1),
(2) Date: Sep. 26, 2016

(87) PCT Pub. No.: WO2015/148985
PCT Pub. Date: Oct. 1, 2015

(65) Prior Publication Data
US 2017/0173041 A1 Jun. 22, 2017

Related U.S. Application Data

(60) Provisional application No. 61/972,125, filed on Mar. 28, 2014.

(51) Int. Cl.
*A61K 9/127* (2006.01)
*A61K 31/553* (2006.01)

(52) U.S. Cl.
CPC ............ *A61K 31/553* (2013.01); *A61K 9/127* (2013.01); *A61K 9/1271* (2013.01); *A61K 9/1278* (2013.01)

(58) Field of Classification Search
CPC .. A61K 31/553; A61K 9/1271; A61K 9/1278; A61K 9/127
See application file for complete search history.

(56) References Cited

U.S. PATENT DOCUMENTS 5,622,713 A * 4/1997 Mehlhorn ............ A61K 9/1278
264/4.3
5,676,928 A 10/1997 Klaveness et al.
5,939,096 A * 8/1999 Clerc ................... A61K 9/1278
424/450
2004/0156889 A1* 8/2004 Hu ........................ A61K 9/127
424/450
2011/0159079 A1 6/2011 Li et al.

FOREIGN PATENT DOCUMENTS

WO WO-2013/086526 A1 6/2013

OTHER PUBLICATIONS

Haran, G. et al. (Sep. 19, 1993). "Transmembrane ammonium sulfate gradients in liposomes produce efficient and stable entrapment of amphipathic weak bases," *Biochim Biophys Acta* 1151(2):201-215.
Hashimoto, K. et al. (Jun. 1976). "Plasma immunoassayable ACTH levels during and after hydrocortisone infusion in patients with Cushing's disease," *Endocrinol. Japon.* 23(3): 243-249.
International Search Report dated Jul. 7, 2015, for PCT/US2015/023109, filed Mar. 27, 2015, 5 pages.
Madden, T. et al. (Mar. 1990). "The accumulation of drugs within large unilamellar vesicles exhibiting a proton gradient: a survey," *Chem Phys Lipids* 53(1):37-46.
Mukthavaram, R. et al. (2013, e-published Oct. 21, 2013). "High-efficiency liposomal encapsulation of a tyrosine kinase inhibitor leads to improved in vivo toxicity and tumor response profile, *Int J Nanomedicine* 8:3991-4006.
Stensrud, G. et al. (Apr. 5, 2000). "Formulation and characterisation of primaquine loaded liposomes prepared by a pH gradient using experimental design," *Int J Pharm* 198(2):213-228.
Tchaikowsky, K. (May 26, 1994). "Protein kinase C inhibitors suppress LPS-induced TNF production in alveolar macrophages and in whole blood: the role of encapsulation into liposomes," *Biochim Biophysica Acta* 1222(1):113-121.
Written Opinion dated Jul. 7, 2015, for PCT/US2015/023109, filed Mar. 27, 2015, 5 pages.
Yamauchi, M. et al. (Jul. 2005). "Reducing the impact of binding of UCN-01 to human alpha1-acid glycoprotein by encapsulation in liposomes," *Biol Pharm Bull* 28(7):1259-1264.
Yamauchi, M. et al. (Mar. 3, 2008). "Controlled release of a protein kinase inhibitor UCN-01 from liposomes influenced by the particle size," *Int J Pharm* 351(1-2):250-258.

* cited by examiner

Primary Examiner — Snigdha Maewall
(74) Attorney, Agent, or Firm — Edward D. Grieff; Mintz, Levin, Cohn, Ferris, Glovsky and Popeo, P.C.

(57) ABSTRACT

Provided herein are compositions methods of using liposomally encapsulated therapeutic drugs, such as staurosporine. Further provided herein are methods of using the liposome compositions to treat a cancer.

14 Claims, 12 Drawing Sheets

Specification includes a Sequence Listing.

LIPOSOMAL DRUG ENCAPSULATION

RELATED APPLICATIONS

This application is a national stage application, filed under 35 U.S.C. § 371, of International Application No. PCT/US2015/023109, filed on Mar. 27, 2015, which claims benefit of priority under 35 U.S.C. § 119(e) to U.S. Provisional Application No. 61/972,125 filed Mar. 28, 2014, the disclosure of each of which is incorporated by reference in its entirety.

STATEMENT AS TO RIGHTS TO INVENTIONS MADE UNDER FEDERALLY SPONSORED RESEARCH AND DEVELOPMENT

This invention was made with government support under CA023100 awarded by the National Institutes of Health. The Government has certain rights in the invention.

INCORPORATION BY REFERENCE OF SEQUENCE LISTING

The contents of the text file named 48537_541001WO_ST25.txt, which was created on Mar. 26, 2015 and is 4.32 KB in size, are hereby incorporated by reference in their entireties.

BACKGROUND OF THE DISCLOSURE

Liposome-based drug carriers can effectively enhance drug efficacy while reducing toxicity, and they have considerable potential as drug delivery platforms in cancer (Drummond, D. C. et al, *Pharmacol. Rev.* 1999, 51 (4), 691-743; Allen, T. M.; Cullis, P. R., *Science* 2004, 303 (5665), 1818-22). Examples include liposomal doxorubicin, and liposomal cytarabine, both FDA approved for cancer treatment (Gabizon, A. et al. *J Control Release* 1998, 53 (1-3), 275-9; Bomgaars, L. et al., *J Clin. Oncol.* 2004, 22 (19), 3916-21). However, a key and pervasive obstacle is that many clinically promising drug classes are difficult to stably encapsulate within liposomes (Fritze, A. et al., *Biochem Biophys Acta* 2006, 1758 (10), 1633-40; Haran, G. et al., *Biochim Biophys Acta* 1993, 1 151 (2), 201-15).

Staurosporine is a pan protein kinase inhibitor with potent anticancer activity in vitro, but clinical use of this compound is precluded by plasma protein binding with rapid clearance, and non-selective toxicity (Gurley L R et al., Staurosporine analysis and its pharmacokinetics in the blood of rats; Los Alamos National Laboratory; Los Alamos, July 1994). These limitations could conceivably be circumvented by liposomal encapsulation and preferential delivery to tumor tissue, but efficiently loading staurosporine or its analogues into liposomes has thus far not been feasible (Yamauchi, M. et al., *Biol Pharm. Bull* 2005, 28 (7), 1259-64).

Staurosporine avidly targets the PKC family of signaling proteins in addition to other kinases such as PKA and PKG, which play a key role in tumorigenesis (da Rocha, A. B. et al., *Oncologist* 2002, 7 (1), 17-33; Sato, W. et al., *Biochem Biophys Res Commun* 1990, 173 (3), 1252-7; Satake, N. et al., *Gen Pharmacol* 1996, 27 (4), 701-5). Staurosporine treatment has been proposed for glioblastoma, a lethal cancer for which current treatments are of limited benefit and have serious toxicity (Wen, P. Y. et al., *N Engl J Med* 2008, 359 (5), 492-507; Stupp, R. et al., *J Clin Oncol* 2007, 25 (26), 4127-36). However, high staurosporine doses would be required to exceed plasma α1-acid glycoprotein (hAGP) binding effects and allow sufficient free drug for antitumor activity (Fuse, E. et al., *Cancer Res* 1998, 58 (15), 3248-53), This level of dosing would cause unacceptable toxicity from pan kinase inhibition in normal tissues.

A potential solution to the obstacles hindering further development of staurosporine and its analogues is offered by liposomal encapsulation because: first, liposomes offer improved circulation half-life by shielding payload from plasma hAGP proteins, and they slow hepatic-renal clearance due to optimal sizing combined with PEGylation; and secondly, leaky microvasculature at tumors and metastases facilitates preferential delivery of liposomal payload to tumor tissue, a selective effect called enhanced permeability retention (EPR) that significantly bypasses the blood brain barrier (BBB) and which can be enhanced by tumor cell/vessel targeting of the carrier liposomes (Wang, A. Z. et al., Nanoparticle Delivery of Cancer Drugs. *Annu Rev Med* 2011; Simberg, D. et al., *Biomaterials* 2009, 30 (23-24), 3926-33).

Various liposomal remote loading methods incorporating chemical and pH gradients have been developed to encapsulate doxorubicin, topotecan and irinotecan (Drummond, D. C. et al., *Cancer Res* 2006, 66 (6), 3271-7; Sadzuka, Y. et al., *J Control Release* 2005, 108 (2-3), 453-9). However, staurosporine encapsulation by liposomes has been poor when attempted with these methodologies (Hashimoto, K. et al., *Endocrinol Jpn* 1976, 23 (3), 243-9; Yarnauchi, M. et al., *Int J Pharm* 2008, 351 (1-2), 250-8).

In addition, the delivery of drugs to only specific sites within the body is one central goal of targeted drug therapy. The concept depends on the differential expression of certain target structures only in a subpopulation of tissues or cell types of the body. Therefore, many groups have tried to elucidate differences in the expression of cell surface markers among different tissue types or between the healthy and diseased state of a tissue or cell. Targeted drug delivery is an attractive concept in particular for cancer chemotherapy, which usually administers highly toxic substances systemically. It is believed that targeted drug delivery primarily to the tumor cells or at least primarily into the vicinity of the tumor cells would allow to either increase the amount of chemotherapeutic, which can be administered at the same level of systemic toxicity hut with an increased effect at the tumor site, or to decrease the amount of chemotherapeutic, which is administered thus lowering the systemic toxicity while still eliciting the same effect at the tumor site.

Targeting of the tumor vasculature, thus, represents a promising new approach for targeted cancer therapy (Matter (2001) *Drug Discov. Today* 6: 1005-1024). Vascular targeting agents are designed to deliver cytotoxic, anti-angiogenic, procoagulant, or proapoptotic substances specifically to the vasculature of tumors. The employed ligands recognize structures associated with tumor blood vessels, i.e., proteins expressed by endothelial cells or associated with the extracellular matrix (Thorpe et al., (2003) *Cancer Res.* 63: 1144-1147; Halin et al. (2001) *News Physiol. Sci.* 16: 191-194), Targeting of the vasculature has several advantages over targeting of tumor cells (Augustin (1998) *Trends. Pharmacol, Sci.* 19: 216-222). There are no physiological barriers as endothelial cells are easily accessible to circulating carrier systems and penetration into the tumor is not necessary. Destruction of few capillary endothelial cells affects a large number of tumor cells depending on them. Since all solid tumors are dependent on neovascularization to grow beyond a few millimeters in diameter, this approach should be broadly applicable. Finally, endothelial cells are genetically stable and do not become resistant to the therapy due to mutation, and only remodeling and expanding endothelium in tumors expresses certain markers such as $\alpha v \beta_3$ and $\alpha v \beta_5$ integrins, that are not expressed by quiescent, healthy, non-tumor vessels. Therefore such markers have been the object of intense investigation as potential anti-tumor targets (see above references).

In addition $\alpha v \beta_3$ and $\alpha v \beta_5$ integrins are also found on different tumor cells including metastatic melanoma cells (Conforti et al. (1992) *Blood* 80: 437-446; Gehlsen et al. (1992) *Clin, Exp. Metastasis* 10: 111-120; Seftor et al. (1999) *Cancer Metastasis Rev.* 18: 359-375 and Varner & Cheresh (1996) *Carr. Opin. Cell. Biol.* 8: 724-730; Nande et al., (2001) *J. Gene Med.* 3: 353-361), Targeting to $\alpha v \beta_3$ and $\alpha v \beta_5$ integrins can be achieved by RGD-containing peptides, with a variety of linear and cyclic RGD-containing peptides (DeNardo et al. (2000) *Cancer Biother. Radiopharm,* 15: 71-79; Pasqualini et al, (1997) *Nat. Biotechn.* 15: 542-546). Several of these RGD-peptides have already been used to deliver radionuclide, proteins, cytotoxic drugs or viral and non-viral carrier systems to integrin-expressing cells in vitro and in vivo (Arab et al. (1998) *Science* 279: 377-380; Schraa et al. (2002) *Int. J. Cancer* 102: 469-475; Jansen et al. (2002) *Cancer Res.* 62: 6146-6151; Erbacher et al. (1999) *Gene Ther.* 6: 138-145; Müller et al. (2001) *Cancer Gene Ther.* 8: 107-117 and Wicknam et al. (1997) *J. Virol.* 170: 8221-8229; Nande et al, (2001) *J. Gene Med.* 3: 353-361).

Therefore, there is a need in the art for the development of methods of producing liposomal drug compositions, wherein the drug (e.g., staurosporine) is stably and efficiently encapsulated and wherein the liposome is efficiently delivered to the drug's specific site of action (e.g., a tumor). The present subject matter as provided herein cures these and other needs in the art by providing, inter alia, methods of making liposomally encapsulated drugs (e.g., staurosporine) and compositions related thereto.

BRIEF SUMMARY OF THE DISCLOSURE

The subject matter provided herein relates to, inter alia, novel methods of making liposomally encapsulated therapeutic drugs, including, for example, staurosporine, or a salt thereof, an analogue thereof, or a salt of an analogue thereof, using reverse pH gradients and internal buffer compositions. Further provided herein are liposome compositions including a therapeutic drug, such as, for example, staurosporine, or a salt thereof, an analogue thereof, or a salt of an analogue thereof, and uses thereof to treat a cancer.

In one aspect, the present subject matter relates to a method of forming a liposomally encapsulated therapeutic drug, such as, for example, a staurosporine composition. The method includes contacting an unloaded liposome that includes an interior cavity having an interior cavity aqueous medium, with an exterior medium (e.g. exterior aqueous medium) having a pH at least about 2 units lower than a pH of the interior cavity and that includes a therapeutic drug. The therapeutic drug (e.g., staurosporine) is allowed to move from the exterior medium (e.g. exterior aqueous medium) to the interior cavity of the unloaded liposome thereby forming a liposomally encapsulated therapeutic drug composition.

In another aspect, a liposome composition is provided. The liposome composition includes a plurality of lipid moieties, wherein the lipid moieties form an interior cavity within the liposome and a therapeutic drug encapsulated within the interior cavity. The interior cavity further includes an interior cavity aqueous medium. The therapeutic drug is present at a lipid:drug ratio of up to 20:1 w/w, or up to 15:1 w/w.

In another aspect, a pharmaceutical composition of the lipid compositions described herein is prepared according to the methods provided herein.

In a further aspect, a pharmaceutical composition prepared according to the methods is provided herein, wherein the liposome is conjugated to a targeting moiety.

In another aspect, a method of treating a cancer in a subject in need thereof is provided. The method includes administering to the subject a therapeutically effective amount of a pharmaceutical composition or a liposome composition described herein and prepared according to the methods provided herein.

In another aspect, a method of treating a cancer in a subject in need thereof by administering to the subject a pharmaceutical composition and/or a liposome composition comprising a therapeutically effective amount of a staurosporine conjugated to a targeting moiety is provided.

BRIEF DESCRIPTION OF THE DRAWINGS

FIG. 1A shows the size (diameter, nm) of the staurosporine liposomes as measured by differential light scattering (DLS). FIG. 1B provides representative scanning electron microscope (SEM) images showing the spherical structure, integrity and diameter of the staurosporine liposomes. The size bar in the right of the image is 100 nm.

FIG. 2A provides the encapsulation efficiency with the internal buffer pH at 3 and at 7.4 compared with the external buffer constant at pH=3, When a gradient existed encapsulation increased by 14 fold. FIG. 2B shows the effect of different internal buffers on encapsulation when the internal pH was 7.4 and external was 3. Ammonium phosphate 300 mM was associated with the highest measured encapsulation efficiency, while ammonium sulfate was close. Sodium salt buffers led to poor encapsulation. FIG. 2C shows the effect of external buffer pH when the internal buffer was held constant at pH 7.4. When the external buffer, either HEPES or PBS, was pH 3, encapsulation efficiency approached 70%.

FIG. 5A shows results for cell line A172, FIG. 5B shows results for cell line U251, FIG. 5C shows results for cell line U118, FIG. 5D shows results for cell line U87, FIG. 5E shows results for the freshly derived line GBM4, and FIG. 5F shows results for the freshly derived line GBM8. EC50 values are indicated for encapsulated and free staurosporine.

FIG. 6A shows U87 glioblastoma cells were implanted s.c. in nude mice. When tumors were established and had reached volumes of 40-50 mm³ the mice were sorted into a treatment and a control group, which had the same mean tumor volume. The treatments were then initiated: control (♦), staurosporine liposomes (■) was injected at 1 mg/kg/dose i.v. three times per week for three weeks, x-axis represents days after tumor implantation. The data show that the encapsulated staurosporine was not removed from the circulation before it could exert a robust antitumor effect. FIG. 6B shows that after three weeks staurosporine treated mice were not treated for 5 weeks. Tumors were reestablished in those mice and after reaching 120 mm³ treatments were administered: control (♦), staurosporine liposomes (■) was injected at 1 mg/kg/dose i.v three times a week for one week, the x-axis represents days after starting the treatment. Even with limited dosing during the first post-growth week, very large tumors, and a two week observation period, the staurosporine liposomes still exerted a clear antitumor effect. FIG. 6C shows liposomal staurosporine had no effect on body weight. Mean body weight for the mouse groups treated with PBS or encapsulated staurosporine before and after the first round of treatment is shown. The bars are means with standard error of the mean (SEM). Unpaired, parametric t-test comparisons indicated no significant difference between weights taken before versus after treatment (PBS p=0.5 Liposomal staurosporine p 0.87).

FIG. 9D).

FIG. 10A shows sections of normal brain area with liposomes only in small vessels, while FIG. 10B shows the liposomes in surrounding tumor tissue.

FIG. 11A shows results for cell line M21 indicative of melanoma, and FIG. 11B shows results for cell line A549, indicative of lung cancer. The MTT Cell viability assay of staurosporine liposomes and free staurosporine was performed in the indicated cell lines. The experiments were carried out in triplicate with data represented as the mean±SEM.

DETAILED DESCRIPTION OF THE DISCLOSURE

Figure 1A:
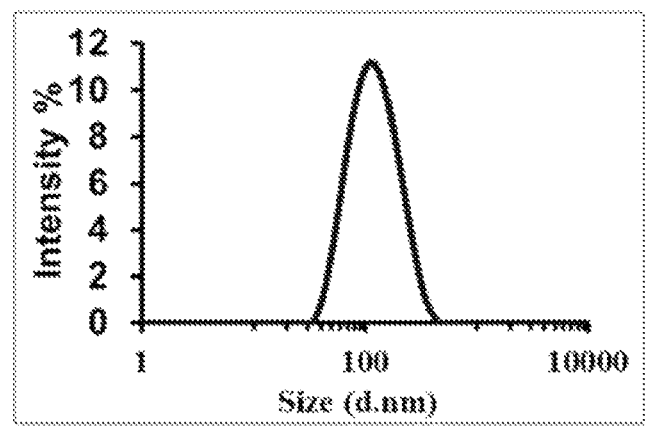
FIGS. 1A-B show liposomes containing staurosporine were of favorable size and charge.

Provided herein are, inter alia, liposomal compositions of therapeutic drugs and methods of encapsulating therapeutically effective amounts of a therapeutic drug (e.g., staurosporine, or a salt thereof, an analogue thereof, or a salt of an analogue thereof) in a liposome using pH gradient reversal. Further provided herein are methods of treating a cancer, particularly a brain cancer, using these liposomal compositions.

The following definitions are provided for the purpose of understanding the present subject matter and for constructing the appended patent claims. Abbreviations used herein have their conventional meaning within the chemical and biological arts.

The phrases "therapeutic drug", "active pharmaceutical ingredient", "API" and the like refer to the active ingredient of a drug product. An API is typically a chemical substance or mixture of chemical substances. Such substances are intended to furnish pharmacological activity or other direct effect in the diagnosis, cure, mitigation, treatment or prevention of disease or to affect the structure and function of the body of a subject, "Drug product" refers, in the customary sense, to a composition useful in the diagnosis, cure, mitigation, treatment or prevention of a disease or disorder in the healing arts, e.g., medical, veterinary, and the like. Further to any aspect disclosed herein, in some embodiments the composition is a pharmaceutical composition suitable for use as a drug product.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound.

As used herein, the term "salt" refers to acid or base salts of the compounds used herein. Illustrative but non-limiting examples of acceptable salts are mineral acid (hydrochloric acid, hydrobromic acid, phosphoric acid, sulfuric acid, and the like) salts, organic acid (acetic acid, propionic acid, glutamic acid, citric acid, and the like) salts, and quaternary ammonium (methyl iodide, ethyl iodide, and the like) salts.

"Patient," "subject," "patient in need thereof," and "subject in need thereof" are herein used interchangeably and refer to a living organism suffering from or prone to a disease of condition that can be treated by administration of a pharmaceutical composition as provided herein. Non-limiting examples include humans, other mammals, bovines, rats, mice, dogs, monkeys, goats, sheep, cows, deer, and other non-mammalian animals. In some embodiments, a patient is human.

"Disease" or "condition" refers to a state of being or health status of a patient or subject capable of being treated with the compounds or methods provided herein.

"Pharmaceutically acceptable excipient" and "(pharmaceutically acceptable carrier" refer to a substance that aids the administration of active therapeutic agent to and absorption by a subject and can be included in the present compositions without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react any of the compounds or the components of the herein described compositions. One of skill in the art will recognize that other pharmaceutical excipients are useful herein.

The term "preparation" is intended to include the formulation of the therapeutic drug with encapsulating material as a carrier providing a capsule in which the therapeutic drug with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The therapeutic drugs and/or the liposome compositions herein can be administered alone or can be co-administered to the patient. Co-administration is meant to include simultaneous or sequential administration of the components individually or in combination (more than one compound or agent). Thus, the preparations can also be combined, when desired, with other active substances (e.g. to reduce metabolic degradation).

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Bioniater Sci. Polym. Ed.* 7:623-645, 1995; as biodegradable and injectable gel formulations (see, e.g., Gao *Phann. Res.* 12:857-863, 1995); or, as microspheres for oral administration (see, e.g., Eyles, *J. Phann. Pharmacol.* 49:669-674, 1997). In another embodiment, the formulations of the compositions herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the present compositions into the target cells in vivo. (See, e.g., Al-Muhammed, *J. Microencapsul.* 13:293-306, 1996; Choun, *Curr. Opin. Biotechnol.* 6:698-708, 1995; Ostro, *Am. J. Hosp. Phann.* 46:1576-1587, 1989). The compositions can also be delivered as nanoparticles.

Pharmaceutical compositions may include compositions wherein the therapeutic drug (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of therapeutic drug effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any therapeutic drug described herein, the therapeutically effective amount can be initially determined from cell culture assays. Target concentrations will be those concentrations of therapeutic drug(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the therapeutic drug being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "associated" or "associated with" in the context of a substance or substance activity or function associated with a disease means that the disease is caused by (in whole or in part) the substance or substance activity or function, a symptom of the disease is caused by (in whole or in part) the substance or substance activity or function, or a side-effect of the compound (e.g., toxicity) is caused by (in whole or in part) the substance or substance activity or function.

As used herein, the term "cancer" refers to all types of cancer, neoplasm, or malignant tumors found in mammals, including leukemia, carcinomas and sarcomas. Exemplary non-limiting cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitoutinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary non-limiting carcinomas which can be treated with a combination of antineoplastic thiol-binding mitochondrial oxidant and an anticancer agent includeacinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g., mouse or rat) and primates (such as humans). Cancer cell lines are widely understood by those skilled in the art as cells exhibiting phenotypes or genotypes similar to in vivo cancers. Cancer cell lines as used herein include cell lines from animals (e.g., mice) and from humans.

The terms "treating" or "treatment" refers to any indicia of success in the treatment or amelioration of an injury, disease, pathology or condition, including any objective or subjective parameter such as abatement; remission, diminishing of symptoms or making the injury, pathology or condition more tolerable to the patents; slowing in the rate of degeneration or decline; making the final point of degeneration less debilitating; and/or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

A "therapeutically effective amount" or "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science, and Technology of Pharmaceutical Compounding* (1999); Pickar, *Dosage Calculations* (1999); and *Remington: The Science and Practice of Pharmacy,* 20$^{th}$ Edition, 2003, Gennaro, Ed., Lippincott, Williams & Wilkins.

Throughout the description and claims of this specification the word "comprise" and other forms of the word, such as "comprising" and "comprises," means including but not limited to, and is not intended to exclude, for example, other additives, or components.

The term "about" refers to any minimal alteration in the concentration or amount of an agent that does not change the efficacy of a therapeutic agent in preparation of a composition and in treatment of a disease or disorder (e.g., cancer). The term "about" with respect to concentration range of the agents (e.g., therapeutic agents) of the current disclosure also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g., chemical compounds including biomolecules or cells) to become sufficiently proximal to react, interact, or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "liposome" refers to vesicles comprised of one or more concentrically ordered bilayers which encapsulate an aqueous phase. The term liposome includes unilamellar vesicles comprised of a single lipid bilayer and generally having a diameter in the range of about 20 nm to about 400 nm. Liposomes can also be multilamellar, which generally have a diameter in the range of about 1 μm to about 10 μm. In some embodiments, liposomes can include multilamellar vesicles (MLV), large unilamellar vesicles (LUV), and small unilamellar vesicles (SUV). In some embodiments, liposomes of the present disclosure have a largest dimension in the range of about 20 nm to about 10 urn, e.g., the range largest dimension is in the range of about 20 nm to about 400 nm, or in the range of about 1 μm to about 10 μm.

The term "encapsulation" as used herein, refers to encircling an internal phase typically resulting in an interior cavity separated from an external media. The components of the internal phase/interior cavity are thus "encapsulated" as described herein. As described herein, the encircled, or encapsulated, internal phase is an aqueous phase. The amount of therapeutic drug that is loaded into the interior cavity of the liposome and therefore unavailable to the external media until the liposome is triggered from release would be considered as "encapsulated" within the liposome.

As used herein, the term "lipid" refers to lipid molecules that can include fats, waxes, steroids, cholesterol, fat-soluble vitamins, monoglycerides, diglycerides, triglycerides, phospholipids, sphingolipids, glycolipids, cationic or anionic lipids, derivatized lipids, and the like, as described in detail below. Suitable lipids useful for forming the instant liposomes can be cationic, zwitterionic, neutral, or anionic. Lipids can form micelles, monolayers, and bilayer membranes. The lipids can self-assemble into liposomes. That is, a plurality of lipids, or multiple lipids, can join together to form liposomes.

"Staurosporine" as provided herein is a natural alkaloid having the systematic IUPAC name: (9S, 10R, 11R, 13R)-2,3,10,11,12,13-Hexahydro-10-methoxy-9-methyl-11-(methylamino)-9,13-epoxy-1H,9H-diindolo[1,2,3-gh:3',2'r-lm]pyrrolo[3,4-j][1,7]benzodiazonin-1-one. In the customary sense, staurosporine refers to CAS Registry No. 62996-74-1. In some embodiments, the staurosporine may be present as an aqueous medium drug salt, such as staurosporine citrate, and/or as an interior cavity drug salt, such as staurosporine phosphate or staurosporine sulfate. In other embodiments, an analogue of staurosporine may be present. Non-limiting examples of such staurosporine analogues include UCN01, Ro 31-8220, and CGP 41251.

As used herein, a "targeting moiety" refers to a chemical or biological moiety (e.g. small molecule, amino acid, peptide, protein, antibody, nucleic acid, or polynucleotide) bound to a liposome described here that delivers or directs the liposome to a particular site, such as a particular cell, organ, or area within an organism. In embodiments, the target moiety is a moiety which enables a liposome to a tumor (e.g. "tumor targeting moiety). In certain aspects, targeting moieties include the "RGD" triad (e.g. a RGD targeting moiety), which includes peptide ligands containing the Arginine-Glycine-Aspartate (RGD) combination. Cell surface receptors that recognize RGD sequences have been grouped into a superfamily of related proteins designated "integrins". Binding of "RGD peptides" to cell surface integrins will promote cell-surface retention, and ultimately translocation, of the polypeptide. Accordingly, any reference to a "RGD targeting moiety" herein refers to any peptide ligand containing this Arginine-Glycine-Aspartate combination which is conjugated to the liposomes described herein.

I. Liposomes

Provided herein are liposome compositions including a plurality of lipid moieties, wherein said lipid moieties form an interior cavity within said liposome. A therapeutic drug is encapsulated within the interior cavity, wherein the interior cavity further includes an interior cavity aqueous medium. The therapeutic drug is present at a lipid:drug weight ratio of up to 20:1 w/w, or up to 15:1 w/w.

The present liposomes include a compartment enclosed by at least one lipid bilayer. The compartment enclosed by a lipid bilayer is referred to herein as an "interior cavity", with an aqueous fluid typically contained in the compartment enclosed by the lipid bilayer, referred to herein as an "interior cavity aqueous medium." When lipids that include a hydrophilic headgroup are dispersed in water they can spontaneously form bilayer membranes referred to as lamellae. The lamellae are composed of two monolayer sheets of lipid molecules with their non-polar (hydrophobic) surfaces facing each other and their polar (hydrophilic) surfaces facing the aqueous medium.

Among the liposomes contemplated herein include unilamellar vesicles comprised of a single lipid bilayer, and generally having a diameter (e.g., largest dimension) in the range of about 20 to about 400 nm, about 50 to about 300 nm, or about 100 to about 200 nm. In some embodiments, the liposome has a diameter from about 20 nm to about 400 nm, from about 40 nm to about 400 nm, from about 60 nm to about 400 nm, from about 80 nm to about 400 nm, from about 100 nm to about 400 nm, from about 120 nm to about 400 nm, from about 140 nm to about 400 nm, from about 160 nm to about 400 nm, from about 180 nm to about 400 nm, from about 200 nm to about 400 nm, from about 220 nm to about 400 nm, from about 240 nm to about 400 nm, from about 260 nm to about 400 nm, from about 280 nm to about 400 nm, from about 300 nm to about 400 nm, from about 320 nm to about 400 nm, from about 340 nm to about 400 nm, from about 360 nm to about 400 nm, or from about 380 nm to about 400 nm. In other aspects, the liposome has a diameter from about 20 nm to about 120 nm, from about 30 nm to about 120 nm, from about 40 nm to about 120 nm, from about 50 nm to about 120 nm, from about 60 nm to about 120 nm, from about 70 nm to about 120 rum from about 80 nm to about 120 nm, from about 90 nm to about 120 nm, from about 100 nm to about 120 nm, from about 40 nm to about 110 nm, from about 50 nm to about 110 nm, from about 60 nm to about 110 nm, from about 70 nm to about 110 nm, from about 80 nm to about 110 nm, from about 90 nm to about 110 nm, or from about 40 nm to about 60 nm. In another aspect, the liposome has a diameter of about 90 nm to about 100 nm. In a further aspect, the liposome has a diameter of about 50 nm to about 100 nm. In some aspects, the liposome has a diameter (e.g., largest dimension) of about 20, about 50, about 40, about 60, about 80, about 90, about 100, about 120, about 140, about 160, about 180, about 200, about 220, about 240, about 260, about 280, about 300, about 320, about 340, about 360, about 380, or about 400 nm.

Also among the liposome compositions contemplated herein are multilamellar liposomes, generally having a diameter (e.g., largest dimension) in the range of about 1 μm to about 10 μm. Such multilamellar liposomes typically consist of several (anywhere from two to hundreds) unilamellar vesicles forming one inside the other in diminishing size, creating a multilamellar structure of concentric phospholipid spheres separated by layers of water. Alternatively, multilamellar liposomes consist of many smaller non-concentric spheres of lipid inside a large liposome. In some embodiments, the liposome has a diameter (e.g., largest dimension) from about 1 μm to about 10 μm, from about 2 μm to about 10 μm, from about 3 μm to about 10 μm, from about 4 μm to about 10 μm, from about 0.5 μm to about 10 μm, from about 6 μm to about 10 μm, from about 7 μm to about 10 μm, from about 8 μm to about 10 μm, or from about 9 μm to about 10 μm. In some embodiment, the liposome has a diameter (e.g., largest dimension) of about 1 μm, about 2 μm, about 3 μm, about 4 μm, about 5 μm, about 6 μm, about 7 μm, about 8 μm, about 9 μm, or about 10 μm.

Accordingly, the liposome compositions herein can be comprised of unilamellar or multilamellar liposomes, generally having a diameter in the range of about 20 nm to about 10 μm. The liposome compositions herein can have a diameter filling within any one or more of the diameter ranges as mentioned above.

Liposome compositions can contain any suitable lipid, including cationic lipids, zwitterionic lipids, neutral lipids, or anionic lipids. Suitable lipids can include fats, waxes, steroids, cholesterol, fat-soluble vitamins, monoglycerides, diglycerides, triglycerides, phospholipids, sphingolipids, glycolipids, cationic or anionic lipids, derivatized lipids, and the like.

Suitable phospholipids include but are not limited to phosphatidylcholine (PC), phosphatidic acid (PA), phosphatidylethanolamine (PIE), phosphatidyl glycerol (PG), phosphatidylserine (PS), and phosphatidylinositol (PI), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPE), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidy ethanolamine (SOPE), 1,2-dielaidoyl-sn-glycero-3-phophoethanolamine (transDOPE), and cardiolipin. In some embodiments, the phospholipid is DOPE. In other embodiments, the phospholipid is DSPC. Lipid extracts, such as egg PC, heart extract, brain extract, liver extract, and soy PC, are also useful. In some embodiments, soy PC can include Hydrogenated Soy PC (HSPC). In certain embodiments, the lipids can include derivatized lipids, such as PEGylated lipids. Derivatized lipids can include, for example, DSPE-PEG2000, cholesterol-PEG2000, DSPE-polyglycerol, or other derivatives generally known in the art. In some embodiments, the derivatized phospholipid is DSPE-PEG2000.

Cationic lipids contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3,-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3β-[N—(N',N'-dimethylaminoethane) carbamoyl]cholesterol (DC-Chol), dimethyldioctadecylammonium (DDAB), and N,N-dimethyl-2,3-dioleyloxy-propylamine (DODMA).

The present liposomes may further contain steroids, characterized by the presence of a fused, tetracyclic gonane ring system. Examples of steroids include, but are not limited to, cholesterol, cholic acid, progesterone, cortisone, aldosterone, estradiol, testosterone, and dehydroepiandrosterone. Synthetic steroids and derivatives thereof are also contemplated for use herein. In some embodiments the steroid is cholesterol.

In some embodiments, the liposome compositions herein include one or more lipids that can be a phospholipid, a steroid, and/or a cationic lipid. In some embodiments, the phospholipid is a phophatidylcholine, a phosphatidylglycerol, a phosphatidylethanolamine, a phosphatidylserine, a phosphatidylinositol, or a phosphatidic acid. In some embodiments, the phosphatidylcholine is distearoyl phosphatidyl choline (DSPC). In some embodiments, the phosphatidylethanolamine is dioleoyl phosphatidyl ethanolamine (DOPE). In some embodiments, the phosphatidylethanolamine is distearoyl-phosphatidyl-ethanolamine (DSPE). In some embodiments, the phosphatidylethanolamine is derivatized. In some further embodiments, the derivatized phosphatidylethanolamine is DSPE-PEG(2000). In some embodiments, the steroid is cholesterol.

Liposome compositions described herein may include about ten or fewer types of lipids, or about five or fewer types of lipids, or about three or fewer types of lipids. In certain aspects, the liposome includes four lipids. For example, the lipids are cholesterol, DOPE, DSPC, and DSPE-PEG(2000), potentially having a molar ratio of cholesterol, DOPE, DSPC, and DSPE-PEG(2000) of 6:6:6:1.

Any suitable combination of lipids can be used to provide the present liposomes. The lipid compositions can be tailored to affect characteristics such as leakage rates, stability, particle size, zeta potential, protein binding, in vivo circulation, and/or accumulation in tissues or organs. For example, DSPC and/or cholesterol can be used to decrease leakage from liposomes. Negatively or positively charged lipids, such as DSPG and/or DOTAP, can be included to affect the surface charge of a liposome.

An "unloaded liposome" as provided herein refers to a liposome unilamellar, multilamellar liposome) that does not include the therapeutic drug (e.g., staurosporine) in the interior cavity or otherwise attached or linked to the liposomal structure. As described above, the "interior cavity" of an unloaded liposome refers to the compartment enclosed by at least one lipid bilayer of the liposome and includes an "interior cavity aqueous medium", i.e., an aqueous fluid present in the interior cavity. The interior cavity aqueous medium may be an aqueous salt solution (e.g., an aqueous solution with a buffer), wherein the salt may be an ammonium phosphate, ammonium sulfate, sodium phosphate, or sodium sulfate. One of skill in the ordinary art will immediately recognize that the lipid compositions provided herein may be adjusted to modulate the release properties or other characteristics of the liposomes as required by a given application.

II. Methods of Drug Encapsulation

Methods of making liposomally encapsulated therapeutic drugs are described herein that use reverse pH gradients and internal buffer compositions having a pH profile as described herein. In one aspect, the method includes contacting an unloaded liposome that includes an interior cavity having an interior cavity aqueous medium, with an exterior medium (e.g. exterior aqueous medium) having a pH at least about 2 units lower than a pH of the interior cavity and that includes a therapeutic drug. The therapeutic drug (e.g., staurosporine) is allowed to move from the exterior medium (e.g. exterior aqueous medium) to the interior cavity of the unloaded liposome thereby forming a liposomally encapsulated therapeutic drug composition.

The method includes forming a liposomally encapsulated staurosporine. The method includes contacting an unloaded liposome with staurosporine, a staurosporine analogue, or a pharmaceutically acceptable salt of staurosporine or a staurosporine analogue in an exterior aqueous medium at an exterior aqueous medium pH, wherein the unloaded liposome includes an interior cavity aqueous medium with an interior cavity pH at least 2 units higher than the exterior aqueous medium pH. The staurosporine is allowed to move from the exterior aqueous medium to the interior cavity thereby forming a liposomally encapsulated therapeutic drug.

The interior cavity aqueous medium is composed such that the therapeutic drug (e.g., staurosporine, or a salt thereof, an analogue thereof, or a salt of an analogue thereof) is allowed to move from an exterior aqueous medium to the interior cavity of the liposome, thereby forming a liposomally encapsulated therapeutic drug (e.g., staurosporine). The interior cavity aqueous medium has a pH which facilitates the movement of the therapeutic drug (e.g., staurosporine) from the exterior aqueous medium to the interior cavity (e.g., by facilitating a pH gradient between the interior cavity and the exterior aqueous medium). In some aspects, the interior cavity pH is at least about 2 units (e.g, 2, 3, 4, 5, 6 units) higher than the exterior aqueous medium pH. In some embodiment, the interior cavity pH is from about 5 to about 9. In other embodiments, the interior cavity pH is from about 6 to about 8. In some embodiments, the interior cavity pH is from about 7 to about 8. In other embodiments, the interior cavity pH is from about 7.4 to about 7.6. In some embodiments, the interior cavity pH is from about 5 to about 9, from about 5.5 to about 9, from about 6 to about 9, from about 6.5 to about 9, from about 7 to about 9, from about 7.1 to about 9, from about 7.2 to about 9, from about 7.3 to about 9, from about 7.4 to about 9, from about 7.5 to about 9, from about 7.6 to about 9, from about 7.7 to about 9, from about 7.8 to about 9, from about 7.9 to about 9, from about 8 to about 9, or from about 8.5 to about 9. In some embodiments, the interior cavity pH is approximately about 5, about 5.5, about 6, about 6.5, about 7, about 7.1, about 7.2, about 7.3, about 7.4, about 7.5, about 7.6, about 7.7, about 7.8, about 7.9, about 8, about 8.5, or about 9.

An "exterior aqueous medium" as provided herein refers to an aqueous solution (e.g., an aqueous solution with a buffer) wherein the therapeutic drug (e.g., staurosporine) may be dissolved. Examples of an exterior aqueous medium useful herein include without limitation 4-(2-hydroxyethyl)-1-piperazineethanesulfonic acid (HEPES) and phosphate buffered saline (PBS). In some embodiments, the exterior aqueous medium pH is about 1 to 4. In other embodiments the exterior aqueous medium pH is about 2 to 4. In some embodiments, the exterior aqueous medium pH is about 2.5 to 3.5. In some embodiments, the exterior aqueous medium pH is about 3. In some embodiments, the exterior aqueous medium pH is about 1 to 4, is about 1.5 to 4, is about 2 to 4, is about 2.5 to 4, is about 3 to 4, is about 3.1 to 4, is about 3.2 to 4, is about 3.3 to 4, is about 3.4 to 4, is about 3.5 to 4, is about 3.6 to 4, is about 3.7 to 4, is about 3.9 to 4, or is about 3.9 to 4. In some embodiments, the exterior aqueous medium pH is about 1, about 1.5, about 2, about 2.5, about 3, about 3.1, about 3.2, about 3.3, about 3.4, about 3.5, about 3.6, about 3.7, about 3.8, about 3.9, or about 4.

In some embodiments, the therapeutic drug is positively charged in the exterior aqueous medium. In some embodiments, the therapeutic drug has a pKa at least 2 units higher than the exterior aqueous medium pH. In some embodiments, the pKa is at least 2.5 units higher than the exterior aqueous medium pH. In some embodiments, the pKa is at least 3 units higher than the exterior aqueous medium pH. In some embodiments, the pKa is at least 3.5 units higher than the exterior aqueous medium pH. In some embodiments, the pKa is at least 4 units higher than the exterior aqueous medium pH. In some embodiments, the pKa is at least 4.5 units higher than the exterior aqueous medium pH. In some embodiments, the pKa is at least 5 units higher than the exterior aqueous medium pH. In some embodiments, the pKa is at least 5.5 units higher than the exterior aqueous medium pH. In some embodiments, the pKa is at least 6 units higher than the exterior aqueous medium pH. In some embodiments, the pKa is at least 6.5 units higher than the exterior aqueous medium pH. In some embodiments, the pKa is at least 7 units higher than the exterior aqueous medium pH. In some embodiments, the pKa is at least 7.5 units higher than the exterior aqueous medium pH. In some embodiments, the pKa is at least 8 units higher than the exterior aqueous medium pH. In some embodiments, the pKa is at least 8.5 units higher than the exterior aqueous medium pH. In some embodiments, the pKa is at least 9 units higher than the exterior aqueous medium pH. In some embodiments, the pKa is at least 10 units higher than the exterior aqueous medium pH. In some embodiments, the pKa is at least 10.5 units higher than the exterior aqueous medium pH. In some embodiments, the pKa is at least 11 units higher than the exterior aqueous medium pH. In some embodiments, the pKa is about 5 and the exterior aqueous medium pH is about 3.

The methods described herein yield liposomes having a therapeutic drug (e.g., staurosporine) loading efficiency of at least 90%. In some embodiments, the methods described herein yield liposomes having a therapeutic drug (e.g., staurosporine) loading efficiency of at least 95%. In other embodiments, the methods described herein yield liposomes having a therapeutic drug (e.g., staurosporine) loading efficiency of about 100%. In comparison, the previously known staurosporine loading efficiency of Tchaikowsky et al., Biochimica et. *Biophysica Acta* 1222 (1994) 113-121 was about 56%, as shown below in Table 1.

TABLE 1

Differential Loading Efficiency of Staurosporine in Liposomes
(At 30 minutes before use, after column purification)

| Tchaikowsky | Liposomal UCN01 | Present Liposome 1 | Present Liposome 2 |
|---|---|---|---|
| 56% | ≈25% | ≈73% | 95-100% |

Specifically, Table 2 below shows the loading efficiency of staurosporine in liposomes made using various phosphatidylethanolamines (PE).

TABLE 2

| | L-STS with DSPE | | L-STS with DPPE | | L-STS with DMPE | | L-STS with DOPE | |
|---|---|---|---|---|---|---|---|---|
| Theoretical # at loading | | | | | | | | |
| [lipid] mg/ml | 4.139 | | 4.147 | | 4.288 | | 4.581 | |
| [lipid] umole/ml | 5.478 | | 5.621 | | 5.954 | | 6.073 | |
| STS mg/ml | 0.23 | | 0.236 | | 0.250 | | 0.255 | |
| STS umole/ml | 0.493 | | 0.506 | | 0.536 | | 0.547 | |
| STS/lipid (w/w) | 0.056 | | 0.057 | | 0.058 | | 0.056 | |
| STS/lipid (mole/mole) | 0.09 | | 0.09 | | 0.09 | | 0.09 | |
| Loading pH | 3.01 | 7.36 | 3.01 | 7.39 | 3.08 | 7.40 | 3.00 | 7.40 |
| Loading efficiency (%)* | 87 | 74 | 87 | 89 | 92 | 88 | 82 | 84 |
| Microtrac size Distribution** | | | | | | | | |
| Peak #1 (nm/%) | 123.4/62 | | 96.3/100 | | 91.8/100 | | 94.5/100 | |
| Peak #2 (nm/%) | 900.1/38 | | | | | | | |
| Peak #3 (nm/%) | | | | | | | | |

*Loading efficiency is calculated based on: post-SEC HPLC peak area ratio/pre-SEC HPLC peak area ratio (estimated error ±2%)
*Peak area ratio: ratio of HPLC peak areas of staurosporine to cholesterol (internal standard)
*Pre-SEC sample: unloaded staurosporine was not removed by size exclusion chromatography column from staurosporine loaded liposome
*Post-SEC sample: unloaded staurosporine was removed by size exclusion chromatography column from staurosporine loaded liposome
**Particle size data is for unloaded liposomes Further, the therapeutic drug in the liposomes made according to the present methods is storage stable for at least one week.

For the methods and compositions provided herein the therapeutic drug (e.g., staurosporine) may be present in the exterior aqueous medium as an exterior aqueous medium drug salt. The therapeutic drug (e.g., staurosporine) may further be present in the interior cavity of the liposome as an interior cavity drug salt. The exterior aqueous medium drug salt may be citrate. The interior cavity drug salt may be a sulfate or a phosphate. In some embodiments, the therapeutic drug (e.g., staurosporine) is present in the exterior aqueous medium as an exterior aqueous medium drug salt and is present in the interior cavity as an interior cavity drug salt. In some embodiments, the exterior aqueous medium drug salt is citrate. In other embodiments, the interior cavity drug salt is phosphate or sulfate. In other embodiments, the interior cavity drug salt is phosphate. In other embodiments, the interior cavity drug salt is sulfate.

In the methods provided herein a liposomally encapsulated therapeutic drug, a salt thereof, an analogue thereof, or a salt of an analogue thereof, is formed by allowing therapeutic drug (e.g., staurosporine) to move from the exterior aqueous medium surrounding a liposome to the interior cavity of the liposome. The therapeutic drug (e.g., staurosporine) may be loaded into the liposome by imposing a pH gradient across the liposome membrane, such that the liposome interior (i.e., the interior cavity aqueous medium) is more basic than the aqueous medium surrounding the liposome (i.e., the exterior aqueous medium). The exterior aqueous medium contains the therapeutic drug (e.g., staurosporine) as exterior aqueous medium drug salt (e.g., citrate) and has a low pH (e.g., about 1-5). Further, the pKa of the interior aqueous medium drug salt may be at least 2 units higher than the exterior aqueous medium pH. The exterior aqueous medium drug salt may exist in a charged form, have good solubility at a pH of less than 5 and permeate (e.g., rapidly permeate) across the liposome membrane.

Upon reaching the more basic interior cavity aqueous medium, the therapeutic drug (e.g., staurosporine) may be present as an interior cavity drug salt. The interior cavity drug salt may have lower solubility (e.g., low solubility at a pH greater than 6). The interior drug salt may be a charged membrane-impermeable form of the drug thereby driving the continued uptake and retention of the drug in the interior cavity of the liposome. Thus, a concentration gradient may be formed between the exterior aqueous medium containing the highly soluble form of the therapeutic drug and the interior cavity containing the less soluble form of the therapeutic drug (e.g., staurosporine).

In some embodiments, the solubility of the interior cavity aqueous medium drug salt is sufficiently low such that the drug salt precipitates within the interior cavity aqueous medium but not in the exterior aqueous medium. In other embodiments, the interior cavity aqueous medium drug salt forms crystals in the interior cavity of the liposome, Thus, in some embodiments, the exterior aqueous medium drug salt is more soluble in the exterior aqueous medium than the interior cavity drug salt in the interior cavity aqueous medium. In some embodiments, the interior cavity drug salt is in crystalline form and the exterior aqueous medium drug salt is solubilized in the exterior aqueous medium.

The step of allowing the therapeutic drug (e.g., staurosporine) to move from the exterior aqueous medium surrounding a liposome to the interior cavity of the liposome as provided herein may be performed at a temperature above room temperature for a certain amount of time. In some embodiments, the allowing is performed at about 50C. The allowing may be performed at about 50 C for at least 15 minutes. In some embodiments, the allowing is performed for about 20 minutes to about 60 minutes. In some embodiments, the allowing is performed for about 30 minutes to about 60 minutes. In other embodiments, the allowing is performed for about 40 minutes to about 60 minutes. In some embodiments, the allowing is performed for about 50 minutes to about 60 minutes.

In order to provide for efficient loading of the liposome with pharmaceutically effective amounts of therapeutic drug (e.g., staurosporine), the molar ratio of lipid to therapeutic drug (e.g., staurosporine) may be up to 20:1 mol/mol. In some embodiments, the lipid to therapeutic drug (e.g., staurosporine) molar ratio is up to 15:1 mol/mol. In some embodiments, the lipid and the therapeutic drug (e.g., staurosporine) are present at a ratio of up to 14:1 mol of lipid/mol of therapeutic drug (e.g., staurosporine). In some embodiments, the lipid and the therapeutic drug (e.g., staurosporine) are present at a ratio of up to 12.5:1 mol of lipid/mol of therapeutic drug staurosporine). In some embodiments, the lipid and the therapeutic drug (e.g., staurosporine) are present at a ratio of up to 11:1 mol of lipid/mol of therapeutic drug (e.g., staurosporine). In some embodiments, the lipid and the therapeutic drug (e.g., staurosporine) are present at a ratio of up to 10:1 mol of lipid/mot of therapeutic drug (e.g., staurosporine). In some embodiments, the lipid and the therapeutic drug (e.g., staurosporine) are present at a ratio of up to 9:1 mol of lipid/mol of therapeutic drug (e.g., staurosporine). In some embodiments, the lipid and the therapeutic drug (e.g., staurosporine) are present at a ratio of up to 8:1 mol of lipid/mol of therapeutic drug (e.g., staurosporine). In some embodiments, the lipid and the therapeutic drug (e.g., staurosporine) are present at a ratio of up to 7.5:11 mol of lipid/mol of therapeutic drug (e.g., staurosporine). In some embodiments, the lipid and the therapeutic drug (e.g., staurosporine) are present at a ratio of up to 7:1 mol of lipid/mol of therapeutic drug (e.g., staurosporine), in some embodiments, the lipid and the therapeutic drug (e.g., staurosporine) are present at a ratio of up to 6.66:1 mol of lipid/mol of therapeutic drug (e.g., staurosporine). In some embodiments, the lipid and the therapeutic drug (e.g., staurosporine) are present at a ratio of up to 6.25:1 mol of lipid/mol of therapeutic drug (e.g., staurosporine). In some embodiments, the lipid and the therapeutic drug (e.g., staurosporine) are present at a ratio of up to 5.88:1 mol of lipid/mol of therapeutic drug (e.g., staurosporine). In some embodiments, the lipid and the therapeutic drug (e.g., staurosporine) are present at a ratio of up to 5.5:11 mol of lipid/mol of therapeutic drug (e.g., staurosporine). In some embodiments, the lipid and the therapeutic drug (e.g., staurosporine) are present at a ratio of up to 5.25:1 mol of lipid/mol of therapeutic drug (e.g., staurosporine). In some embodiments, the lipid and the therapeutic drug (e.g., staurosporine) are present at a ratio of up to 5:1 mot of lipid/mol of therapeutic drug (e.g., staurosporine).

Similarly, the weight ratio of lipid (quantified in terms of the unloaded liposome particles) to therapeutic drug (e.g., staurosporine) may be up to 20:1 w/w. In some embodiments, the lipid to therapeutic drug (e.g., staurosporine) weight ratio is up to 16:1 w/w. In some embodiments, the lipid and the therapeutic drug (e.g., staurosporine) are present at a ratio of up to 15:1 w/w of lipid/therapeutic drug (e.g., staurosporine). In some embodiments, the lipid and the therapeutic drug (e.g., staurosporine) are present at a ratio of up to 10:1 w/w of lipid/therapeutic drug (e.g., staurosporine).

This herein described reverse loading methodology offers an advantage in terms of liposomal therapeutic drug (e.g., staurosporine) retention. Prevention of premature release of drug payload by circulating liposomes is an essential requirement, but payload release still has to occur at the tumor site. Contrary to previous gradient loading methods, which only supported the liposomal retention of weakly basic anthracyclines such as doxorubicin and to some extent the campothecin analogues, the reverse pH gradient loading methodology described herein results in stable liposomal therapeutic drug (e.g., staurosporine) encapsulation with essentially all compounds still contained after 3 hours of incubation in human serum. As a result, the liposomal outer shell does not have to be modified by extensive cross-linking and the addition of stabilizers to slow payload efflux. Despite the stable liposomal retention, the therapeutic drug (e.g., staurosporine) should release as required at the tumor site.

III. Liposomal Compositions

Further provided herein are liposomal compositions including therapeutic drug (e.g., staurosporine) or a salt thereof, an analogue thereof, or a salt of an analogue thereof and uses thereof to treat a cancer. The liposomes provided herein may include an interior cavity with a salt of staurosporine (interior cavity drug salt) and an interior cavity aqueous medium. As described above the interior cavity drug salt provided herein may be more soluble at a low pH and is less soluble at a high pH. In one embodiment, the phrase "low pH" refers to a pH of less than 5 and the phrase "high pH" is a pH greater than 6. Where the pH of the interior cavity aqueous medium (i.e., interior cavity pH) is above 6, the interior cavity drug salt may be present in its soluble or its precipitated form. Thus, in one aspect a liposome including an interior cavity with an interior cavity drug salt and interior cavity aqueous medium is provided. In some embodiments, the interior cavity pH is greater than 6. In some further embodiments, the interior cavity pH is about 7 to 8. In some further embodiments, the interior cavity pH is about 7.4 to 7.6. In some further embodiments, the interior cavity drug salt is present in its soluble form. In some further embodiments, the interior cavity drug salt is present in its soluble and its precipitated form. In some further embodiments, the interior cavity drug salt is present in its soluble form. In some other further embodiment, the interior cavity drug salt is present in its crystallized form.

In one aspect, a liposome including an interior cavity with a staurosporine phosphate or staurosporine sulfate and an interior cavity aqueous medium is provided. In some embodiments, the liposome includes an interior cavity aqueous medium with an interior cavity pH of about 6 to 8. In other embodiments, the interior cavity pH is about 7 to 8. In other embodiments, the interior cavity pH is about 7.4 to 7.6. In some embodiments, the staurosporine phosphate or staurosporine sulfate is present in a therapeutically effective amount.

IV. Pharmaceutical Formulations

The methods and compositions provided herein are useful in preparing pharmaceutical liposome compositions. In one aspect, a pharmaceutical composition prepared according to the methods provided herein including embodiments thereof is provided. In some embodiments, the present subject matter can include a liposome composition and a physiologically (i.e., pharmaceutically) acceptable carrier. Typically, the physiologically acceptable carriers are present in liquid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions useful herein (See, e.g., Remington's Pharmaceutical Sciences, 17th ed., 1989).

The present compositions may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized liposome compositions.

The liposome composition of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by oral, intraarticular, intravenous, intramuscular, intratumoral, intradermal, intraperitoneal, and subcutaneous routes, can be prepared. Such formulations can include aqueous and non-aqueous, isotonic sterile injection solutions, which can contain antioxidants, buffers, bacteriostats, and solutes that render the formulation isotonic with the blood of the intended recipient. Formulations for injection can also include aqueous and non-aqueous sterile suspensions that can include suspending agents, solubilizers, thickening agents, stabilizers, and preservatives. Injection solutions and suspensions can also be prepared from sterile powders, granules, and tablets.

The present compositions can be administered, for example, by intravenous infusion, topically, intraperitoneally, intravesically, orally, transdermally, intranasally, intrapulmonary, intravitreally, intraocularly, or intrathecally. Parenteral administration and intravenous administration are the preferred methods of administration. In addition, the present liposomes can be administered via surgical devices, or via the GI or genitourinary tracts. The formulations of liposome compositions can be presented in unit-dose or multi-dose sealed containers, such as ampoules and vials.

Suitable formulations for rectal administration include, for example, suppositories, which includes an effective amount of a packaged liposome composition with a suppository base. Suitable suppository bases include natural or synthetic triglycerides or paraffin hydrocarbons. In addition, it is also possible to use gelatin rectal capsules, which contain a combination of the liposome composition of choice with a base, including, for example, liquid triglycerides, polyethylene glycols, and paraffin hydrocarbons.

The pharmaceutical preparation is preferably in unit dosage form. In such form the preparation is subdivided into unit doses containing appropriate quantities of the active component, e.g., a liposome composition. The unit dosage form can be a packaged preparation, the package containing discrete quantities of preparation. The composition can, if desired, also contain other compatible therapeutic agents.

V. Methods of Treatment

The methods and compositions provided herein are particularly useful in treating cancer generally, as well as one of several specific forms of cancer. In one aspect, a method of treating a cancer in a subject in need thereof is provided. The method includes administering to the subject a therapeutically effective amount of a pharmaceutical composition prepared according to the methods provided herein. In another aspect the method includes administering to the subject a therapeutically effective amount of a liposome composition described herein. In some embodiments, the cancer being treated is brain cancer. In other embodiments, the cancer being treated is selected from the group consisting of brain cancer, pancreatic cancer, breast cancer, lung cancer, bone cancer, a hepatic cancer, and melanoma. In further embodiments, the methods herein involve administering to the subject a therapeutically effective amount of a pharmaceutical composition prepared according to the methods provided herein, specifically targeted to treat a specific organ of the subject, such as the brain, pancreas, breasts, lungs, bones, liver, skin, or any other organ of interest.

The liposome compositions described herein may be administered to a subject in need thereof in a way that they may amass at a given site (target site) in a subject after administration, having ceased to systemically circulate within the subject. As used herein, the phrase "target site" refers to a location at which liposome accumulation and delivery of an active pharmaceutical ingredient is desired. In some cases, the target site can be a particular tissue or cell and may be associated with a particular disease state. In some cases, the accumulation may be due to binding of a specific biomarker at the target site by a liposome comprising a ligand that recognizes the biomarker. In some cases, the liposome accumulation may be due to the enhanced permeability and retention characteristics of certain tissues such as cancer tissues. Liposome accumulation may be assessed by any suitable means, such as compartmental analysis of test subjects or noninvasive techniques such as positron emission tomography or nuclear magnetic resonance imaging. However, one of skill in the art can plan the timing of liposome administration to a particular subject so as to allow for sufficient accumulation at a target site without directly measuring accumulation in the subject.

In another embodiment, the pharmaceutical compositions, and thus the therapeutic drug (e.g., staurosporine, a salt thereof, an analogue thereof, or a salt of an analogue thereof), can be delivered to a specific target site by conjugation to a specific targeting moiety. For example, liposomes herein containing staurosporine can be delivered to a specific tumor target site, or a specific organ target site, either taken alone or after being conjugated to a RGD targeting moiety. RGD targeting moieties mediate tumor-homing through binding to αv integrins, and typically target brain cancer, ovarian cancer, prostate cancer, head and neck cancer, and/or melanoma. Other targeting moieties known as useful in the art for targeting to a specific site of inter such as a cancer site, are further contemplated herein.

In this regard, targeting moieties useful herein will typically target specific surface markers for tumors (targeted using small molecules, short peptides, antibodies, antibody fragments, and/or DNA/RNA aptamers). Such specific surface markers by way of non-limiting example may include CD105 Endoglin, a folate receptor, a transferrin receptor, αvβ33 integrin, galectin-1, tyrosine kinase-7, HER 2/neu, an EGF receptor (EGFR), a galactose receptor, CD44, P32, MUC-1, Claudin-4, an uPA receptor (also called CD87), a Sigma receptor, VEGFR2, a CG receptor, a LH receptor, CD20, CD19, a surface molecule on SCLC cells, CD13/aminopeptidase N, GD2, CD33, αvβ3 and neuropilin-1, prostate specific membrane antigen (PSMA), CD22, BAFF, Antigen A7, a nucleosome, VACM-1, a carcinoembryonic antigen (CEA), cMET, ICAM-1, an E-selectin, a nucleolin, a vitamin H (biotin) receptor, a GPR 120 putative fatty acid receptor, clotting factor VIII expressed in plasma, Tumor associated glycoprotein-72 (TAG-72), AnnA1 (Annexin A1), Endosialin (CD248), Interleukin-11 alpha receptor, NG2, PDFRβ, Plectin-1, a Gastrin Releasing Peptide Receptor (GRPR), Hepsin (HPN), an activated leukocyte adhesion molecule (ALCAM, CD166), an epithelial cell adhesion molecule (EpCAM), Thy-1 or CD90 (Cluster of Differentiation 90), CD74, an IGFR and HER2 receptor, and a fibroblast growth factor receptor (FGFR).

In one embodiment in this regard, the targeting moiety, or RGD-containing peptide, can be attached directly or indirectly to a lipid, which in turn is inserted or incorporated into the present liposomes. Non-limiting examples of potentially suitable lipids in this regard include glycerides, glycerophospholipides, glycerophosphinolipids, glycerophosphonolipids, sphingolipids, phospholipids, isoprenolides, steroids, stearines, steroles, and/or carbohydrate containing lipids. Additional non-limiting examples of lipids for the attachment of the RGD-containing peptides are phospholipids, such as phosphatidylcholine (PC), phosphatidylserine (PS), and phosphatidylethanolamine (PE), in particular distearoylphosphatidyl (DSPE) or alpha-(dipalmitoylphosphatidyl (DPP)) which are often included in liposomes used for delivery of drugs.

In another embodiment the lipid attached to the RGD-containing peptide can be selected from the group consisting of N-caproylamine-PE, N-dodecanylamine-PE, phophatidylthioethanol, N+4-(p-maleirnidomethyl) cyclohexane-carboxamide-PE (N-MCC-PE), N-[4-(p-maleimidophenyl) butyramide]-PE (N-MPB), N-[3-(2-pyridyldithio)propionate]-PE (N-PDP), N-succinyl-PE, N-glutaryl-PE, N-dodecanyl-PE, N-biotinyl-cap-PE, phosphatidyl-(ethylene glycol), PE-polyethylene glycol (PEG)-carboxylic acid, PE-PEG-maleimide, PE-PEG-PDP, PE-PEG-amine, PE-PEG-biotin, PE-PEG-HNS, dipahnitoyl-glycerosuccinyl-lysine, alpha-methoxy-omega-(1,2-dioctadecenoyloxy glyceryl) (DO), and alpha-methoxy-omega-(1,2-ditetradecenoyloxy glyceryl) (DT).

In a further embodiment, the RGD-containing peptide is attached to the staurosporine, a salt thereof an analogue thereof, or a salt of an analogue thereof. The staurosporine can be attached to the RGD-containing peptide in such a way that it is releasable and preferably the release of the staurosporine is primarily effected in the tissues or areas of the body to which the RGD-containing peptide binds, i.e., primarily in tumor endothelium or tumors. Certain means of attachment of the staurosporine are short polypeptide stretches, which are cleavable, for example, by enzymes which are released at the target site. Thus, the staurosporine can be released in the tumor endothelium or in tumors. Enzymes of this type include, for example metalloproteinases. Such releasable connections are known in the art and can be selected to provide a further specificity on top of the specificity already achieved by the target specific binding of the RGD-containing peptide.

In one embodiment of the present compositions, the targeting moiety is integrated into or attached to the liposome, which allows the respective entity to be targeted to specific sites and tissues in the body. The targeting moiety can be attached to one of the components, which are used for the generation of liposomes prior to, during, or after formation of the liposome. In particular for liposomes, it is envisioned that the targeting moiety is integrated into the lipid mono or multilayer of the liposome. In one embodiment, the targeting moiety is primarily comprised on the outer surface of the liposome to allow interaction of the targeting moiety with its target preferably upon administration of the present composition to a patient. In some embodiments the targeting moiety can be attached to between about 0.1 mol % to about 10 mol % of all components which are used for the generation of the liposome.

In this regard, suitable targeting moieties useful herein include any homing peptides that specifically recognize the endothelium of tumor vessels, extravasate, and penetrate deep into the extravascular tumor tissue. The prototypical peptide of this class, the specific RGD-containing peptide iRGD (CRGDKGPDC) (SED ID NO: 1), contains the integrin-binding RGD motif. The tumor-penetrating properties of iRGD are mediated by a second sequence motif, R/KXXR/K (SED ID NO: 2). This C-end Rule (or CendR) motif is active only when the second basic residue is exposed at the C-terminus of the peptide. Proteolytic processing of iRGD in tumors activates the cryptic CendR motif, which then binds to neuropilin-1 activating an endocytic bulk transport pathway through tumor tissue.

Other potentially useful targeting moieties herein, as well as possible targets for the same, include but are not limited to melanoma-homing peptide (-CVNHPAFAC-) (SED ID NO: 3); Cecropin A and B targeting for leukemia and bladder cancer; Pleurocidin targeting for breast cancer; Magainin2 targeting for bladder cancer; a5-a6 Bax peptide; BH3 domain; KLAKLAK (SED ID NO: 4) targeting for glioblastoma; Tat, and NGR (NGR-hTNF) targeting for ovarian cancer, mesothelioma, lung cancer, sarcoma, colon cancer, and/or hepatic cancer.

Additional specific, non-limiting examples of peptides containing targeting moieties useful for targeting various cancers and/or tumors herein are found in Table 3, below.

TABLE 3

Peptides Targeting Tumor Blood Vessels

| Sequence (no. of amino acids, name) (SEQ ID NO) | Tumor types tested | Receptors | Applications |
|---|---|---|---|
| CDCRGDCFC (9, RGD) (SED ID NO: 5) | Various tumor types | $\alpha_v\beta_3$ and $\alpha_v\beta_5$ integrins | Targeted diagnosis and therapy (TD and TT) |
| CNGRCVSGCAGRC (13, NGR) (SED ID NO: 6) CNGRC (5, NGR-2C) (SED ID NO: 7) | Various tumor types | CD13 | TD and TT |
| CTPSPFSHC (9, TCP-1) (SED ID NO: 8) | Orthotopic colorectal cancer and gastric cancer | ND* | TD and TT |
| IFLLWQR (7, IF7) (SED ID NO: 9) | Melanoma Colorectal cancer | Anxa1 | TT |
| CTTHWGFTLC (10) (SED ID NO: 10) | MDA-MB-435-derived breast carcinomas | MMP-2 MMP-9 | TT |
| KDEPQRRSARLSAKP APPKPEPKPKKAPAKK (31, F3) (SED ID NO: 11) | HL-60 human leukemia tumor MDA-MB-435 tumors | Nucleolin | ND |
| CSRPRRSEC (9) (SED ID NO: 12) | HPV16-induced dysplastic skin | ND | ND |
| CGKRK (5) (SED ID NO: 13) and CDTRL (5) (SED ID NO: 14) | HPV16-induced skin carcinoma Breast carcinomas | ND | ND |
| CKAAKNK (7, KAA) (SED ID NO: 15) and CKGAKAR (7, KAR) (SED ID NO: 16) | Pancreatic tumors | ND | ND |
| CRGRRST (7, RGR) (SED ID NO: 17) | Pancreatic tumors Angiogenic islets | PDGF-β | ND |
| CRGDK/RGPD/EC (9, iRGD) (SED ID NO: 18) | Various tumor types | αv integrins and neuropilin-1 | TD and TT |
| CPRECESIC (9) (SED ID NO: 19) | EF43-fgf4-derived breast tumor MDA-MB-435-derived breast tumor | Aminopeptidase A | TT |
| CGNSNPKSC (9, GX1) (SED ID NO: 20) | Gastric cancer | ND | TD and TT |
| SVSVGMKPSPRP (12, SP5-52) (SED ID NO: 21) | Several cancers | ND | TT |

Other specific peptides containing targeting moieties known to be useful in targeting for tumors and/or cancers are fully contemplated as being within the scope of the presently described subject matter.

In therapeutic use for the treatment of cancer, the present liposome compositions, including an effective amount of a therapeutic drug (e.g., staurosporine), can be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the liposome composition being employed. For example, dosages can be empirically determined considering the type and stage of cancer diagnosed in a particular patient. The dose administered to a patient should be sufficient to affect a beneficial therapeutic response in the patient over time. The size of the dose will also be determined by the existence, nature, and extent of any adverse side effects that accompany the administration of a particular liposome composition in a particular patient. Determination of the proper dosage for a particular situation is within the skill of the practitioner. Generally, treatment is initiated with smaller dosages, which are less than the optimum dose of the liposome composition. Thereafter, the dosage is increased by small increments until the optimum effect under circumstances is reached. For convenience, the total daily dosage may be divided and administered in portions during the day, if desired.

Examples

Animal Subjects:

Athymic nu nu mice of either sex, 5-6 weeks of age were used and 5 mice were housed in sterilized cages supplied with purified air passed through activated charcoal and HEPA filters. The mice were provided with autoclaved bedding, food, and water. All animal procedures were conducted in strict accordance with all appropriate regulatory standards under UCSD animal use protocol #S10005 which was reviewed and approved by the UCSD Institutional Animal Care and Use Committee (IACUC).

Cell Culture and Reagents:

A172, U87, U118 and U251 glioblastoma lines were maintained under standard culture conditions in Dulbecco's modified Eagle's medium (DMEM) supplemented with 10% FBS, GBM4 and 8 human tumorspheres were cultured in human basal neural stem cell medium supplemented with EGF, FGF and supplement medium. Dioleoylphosphatidylethanolamine (DOPE), cholesterol, distearoylphosphatidylcholine (DSPC) and mPEG2000 were purchased from Avanti Polar Lipids. Staurosporine was purchased from LC laboratories. Sephadex G50 was purchased from GE healthcare, Sepharose CL6B, DMEM were purchased from Sigma.

Preparation of Liposomes:

The liposome formulation included cholesterol, DOPE, DSPC, DSPE-mPEG2000 (6:6:6:1 molar ratio) in chloroform, and was evaporated under argon gas (Murphy, E. A. et al., Mol Cancer Ther 2011, 10 (6), 972-82). The dried lipid film was hydrated with a buffer containing ammonium phosphate, ammonium sulfate, sodium phosphate, or sodium sulfate (300 mM, 7.4) and vortexed for 1 minute to remove any adhering lipid film. Sonication in a bath sonicator (ULTRAsonik 28X) for 1 minute at room temperature produced multilamellar vesicles (MLV). ME-Vs were then sonicated with a Ti-probe (Branson 450 sonifier) for 2 minutes to produce small unilamellar vesicles (SUV), indicated by the formation of a translucent solution. Extrusion through a 100 nm pore size polycarbonate filter (Whatman) was the final stage of a stepwise series of extrusions to reduce SUV size.

Reverse pH Gradient for Drug Encapsulation:

The prepared liposomes with internal buffer at pH 3 or 7.4 were passed through a Sephadex G-50 column equilibrated with HEPES buffered saline (FIBS; 20 mM HEPES, 150 mM NaCl, pH 7.4) to exchange the external buffer. Staurosporine in 10% citric acid was added to the liposome suspension, and the external buffer pH was changed to 3, 5, or 7.4. The solution was heated at 50 C for 20 minutes, left to stand 4 hours at room temperature, and then applied to a Sephadex G-50 column and eluted with MilliQ water. Encapsulated staurosporine was quantified by measuring absorbance of the liposome suspension at 294 nm on a spectrophotometer, and interpolating concentration from a standard curve of free staurosporine.

Liposome Physical Characterization:

The liposome suspension was diluted in 1/10 in MilliQ water and a 100 µl aliquot was sized using light backscattering (Malvern Zetasizer, ZEN 3600). The same instrument measured particle net charge expressed in mV. Size and surface $\xi$-potential were obtained from three repeat measurements with a backscattering angle of 173°. Liposome morphology and size were further characterized using scanning electron microscopy (SEM). Samples were prepared by applying 5 µl droplets of the liposome suspension onto a polished silicon wafer. After drying the droplets at room temperature overnight, the wafer was coated with chromium, and then imaged on a Philips XL-30 electron microscope to 30,000×.

In Vitro Drug Release Studies:

Staurosporine loaded liposomes were incubated in PBS or human serum at room temperature. The staurosporine concentration remaining in the liposomes was at 0.5, 1, 2, 4, 6, 12, 24, 48, and 72 hours. Separation of the liposomes from both PBS and serum was performed by size exclusion chromatography (SEC). The PBS liposome suspension was applied to a Sephadex G-50 column, while a sepharose CL6B column was used for serum, both eluted with PBS (Yamauchi, M. et al., Int J Pharm 2008, 351 (1-2), 250-8). After separation the concentration of staurosporine within liposomes incubated in PBS was determined spectrophotometrically at 294 nm. The liposomes separated from serum were lyophilized, dissolved in HPLC grade methanol, centrifuged, and the supernatant collected following by evaporation. The evaporation residue was dissolved in 100% HPLC grade acetonitrile, and HPLC (Agilent HPLC) performed using a 70% acetonitrile-water mobile phase to measure staurosporine.

Activity of Encapsulated Staurosporine Against Glioblastoma Cells in Vitro:

Applicants evaluated the cytotoxic effect of staurosporine encapsulating liposomes and free staurosporine on a range of established human glioblastoma cell lines including A172, U251, U118, and U87 cells. All cells were grown in 96 well plates in complete medium with 10% FBS at 37 C, and then either free staurosporine or staurosporine liposomes were added and the cells incubated for another 72 hours. Applicants also established human glioblastoma cancer stem cells from fresh surgical isolates using stem cell media methods as previously reported and tested staurosporine cytotoxicity with these lines. For the experiments with free staurosporine, 10 mmol/L stocks were first serially diluted in DMSO then with medium, to avoid precipitation. Cell viability was quantified using the MTT assay (Rajesh, M. et al, J Am Chem Soc 2007, 129 (37), 11408-20). Briefly, the absorbance at 540 nm was measured after adding MTT (Sigma-Aldrich). Results were expressed as percent viability=[A540(treated cells−background/A540(untreated cells)−background]×100%. Dose-response curves were plotted using GraphPad® Prism software and EC50 values were calculated.

In Vivo Activity of Encapsulated Staurosporine Measured with Flank Tumor Model:

Athymic nu/nu mice 5-6 weeks old were subcutaneously inoculated in the right and left flanks with 4 million U87 cells, and the resultant tumors were allowed to grow to 40-50 mm³. The mice were sorted so that the treatment and control groups had the same average tumor size. Mice were injected intravenously with liposomally encapsulated staurosporine, or with PBS; it should be noted that free staurosporine is cleared immediately, and the doses required to bypass this effect are acutely toxic. The encapsulated staurosporine groups received a 0.8 mg/kg staurosporine dose 3 times per week for 3 weeks. The tumors were measured weekly using calipers and volume was calculated using the standard formula, V=(Length×[Width²])/2. The mice were sacrificed when the tumors attained 1500 mm³. Body weights were measured before and after 3 weeks of treatment.

Recurrent Tumor Study with Encapsulated Staurosporine:

To confirm that suppression of tumor growth was due to treatment with liposomal staurosporine and not an artifact from failure of the tumors to thrive, the treatment was stopped at 3 weeks in the encapsulated staurosporine group, and the tumors allowed to regrow over a 5 week period. When the tumors reached 120 mm³, treatment was resumed for one week during which three IV doses of either PBS, or encapsulated staurosporine at 0.8 mg/Kg, were given. The tumors were measured weekly for the next two weeks, and then the mice were sacrificed in accordance with Applicants' IACUC protocol. Body weights were taken before and after this second treatment course.

Figure 10A:
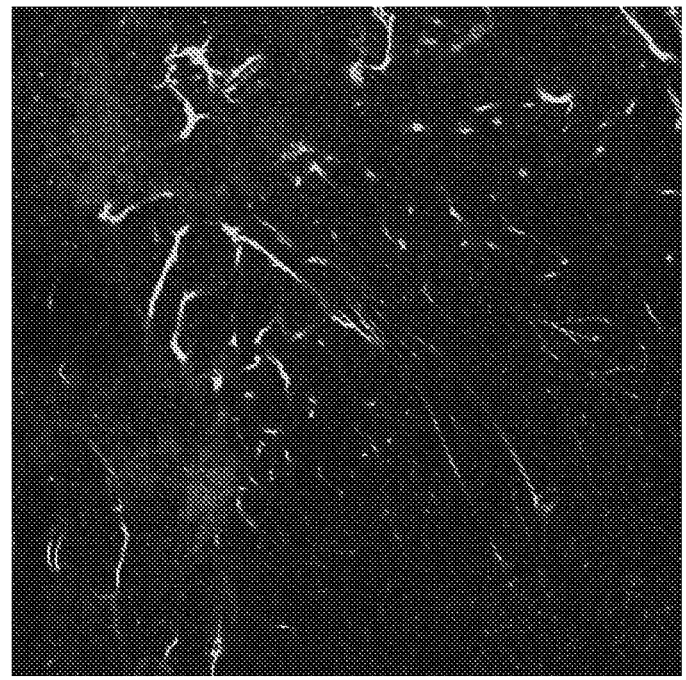
FIGS. 10A-B shows confocal microscopy results for sections of the tumor area from mice in an orthotopic model for brain cancer.
Figure 10B:
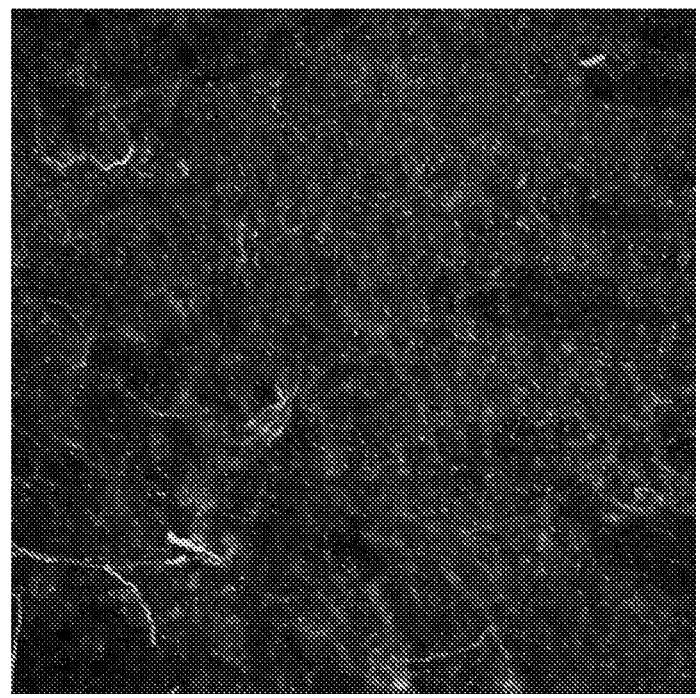
Figure 11A:
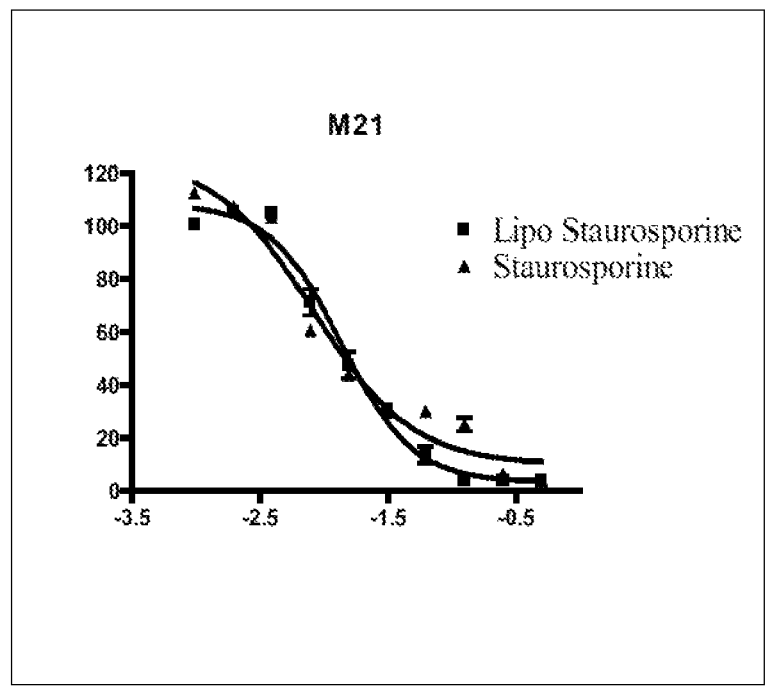
FIGS. 11A-B show $EC_{50}$ values for encapsulated and free staurosporine in vitro in different cell lines.
Figure 11B:
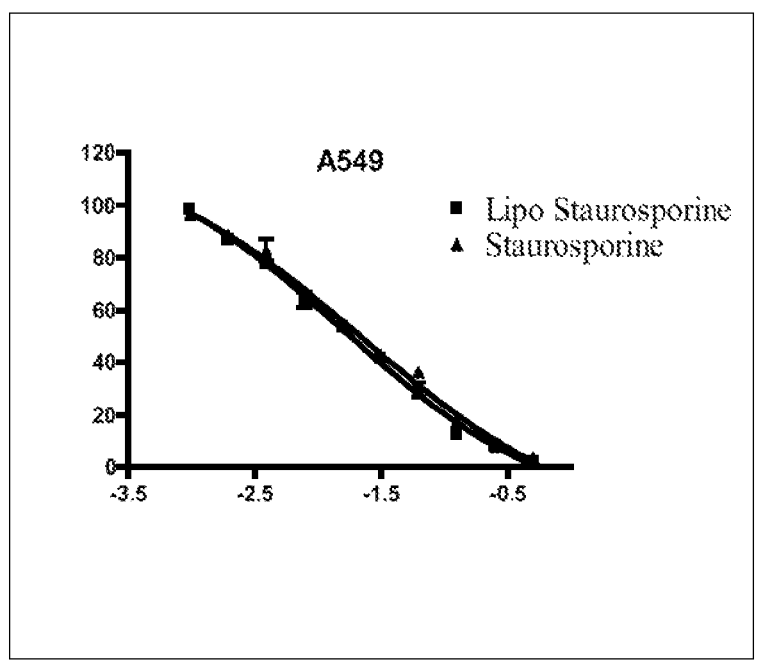

In Vivo Activity of Encapsulated Staurosporine Measured with Orthotopic Brain Tumor Model:

Nude balb/c mice (age 6 weeks) were injected intracranially using a stereotactic apparatus with 200,000 GBM18 patient-derived neurosphere cells. After 9 days later groups of 10 mice were randomized into 3 arms: 1) control (PBS), 2) LSTS (0.8 mg/kg), or 3) RGD-LTS (0.8 mg/kg) and treated 3×/week for 3 weeks (total for 9 doses), Mice were followed until neurological symptoms and sacrificed. Mice from this study that became sick were treated with BoDipy labeled-LSTS (red) i.v., after 4 hours fluorescein-labeled *G. simplicifolia* lectin was injected i.v. which binds selectively to mouse endothelial cells, and sacrificed after 15 minutes. Fresh unperfused brains were removed and confocal microscopy was done using Nikon eclipse Ti confocal microscope. Sections of tumor area shows liposomes (red) in small vessels (FIG. 10A) as well as in surrounding tumor tissues (FIG. 10B).

1. Results

Figure 1B:
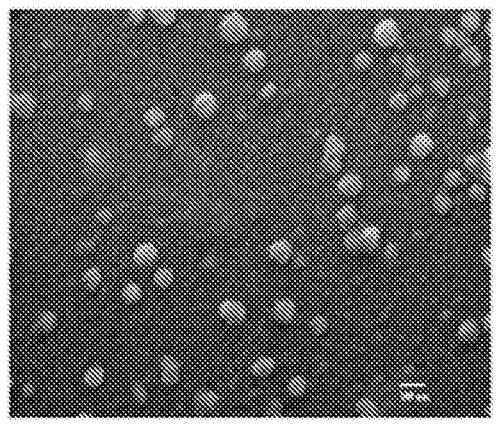

Liposome Physical Characterization:

The average liposomal size was 108±1.1 nm (three measurements), the zeta potential or net charge was close to the desired neutrality at 2.18±2.4 (ten measurements). SEM data confirmed that the staurosporine loaded liposomes were spherical, intact and averaged approximately 108 nm in diameter (FIGS. 1a and 1b).

Figure 2A:
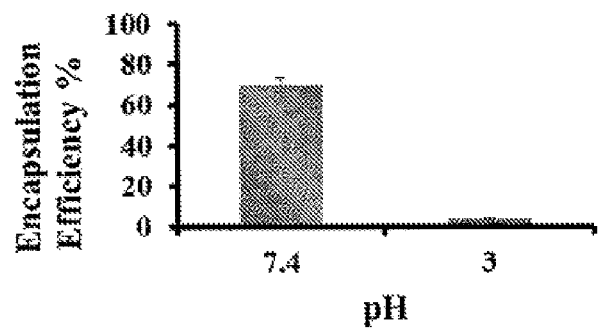
FIGS. 2A-C demonstrate the effect of pH on staurosporine encapsulation efficiency.
Figure 2B:
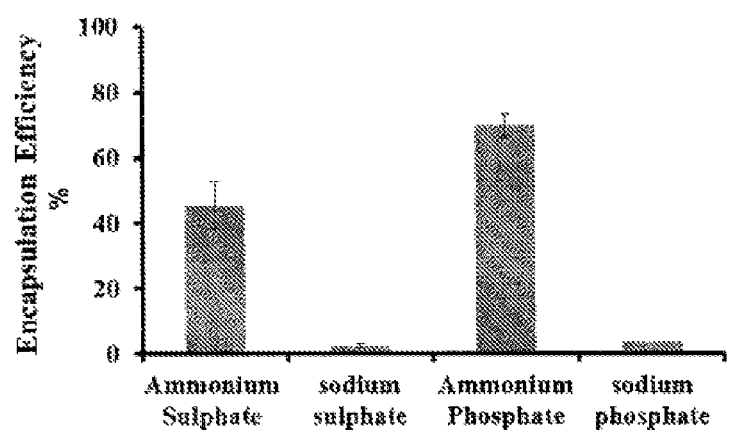
Figure 2C:
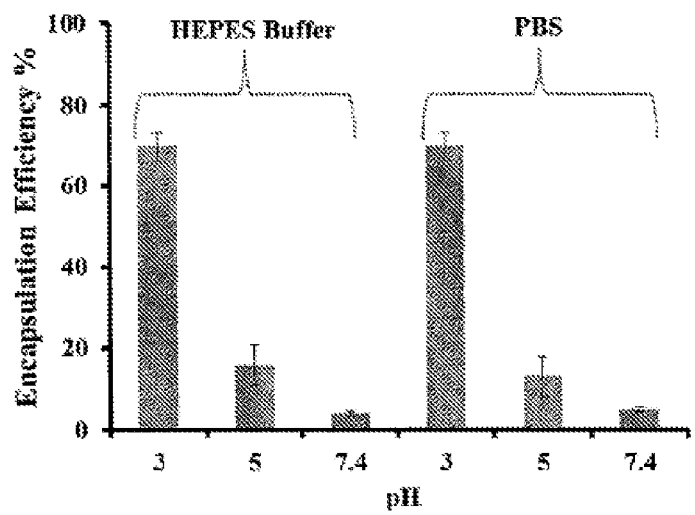

Encapsulation Efficiency:

Reverse pH Gradient with Ammonium Based Buffers Produced Effective Encapsulation:

FIG. 2a shows the effect of internal pH and FIG. 2b shows the effects of internal buffer composition. Consistent with previous reports, Applicants obtained poor loading of staurosporine (~5%) with an internal pH of 3 and external pH of 7.4 (FIG. 2c). Internal pH levels of 5 with an external pH of 7.4 also resulted in very low encapsulation rates. The best encapsulation efficiencies were achieved when the internal buffer pH was 7.4 and was based on ammonium phosphate, or ammonium sulfate, with rates of 70% and 65%, respectively, while sodium phosphate and sodium sulfate produced very low encapsulation of 3-4% (FIGS. 2a, 2b, and 2c). Externally, HEPES and PBS buffers were associated with the same encapsulation efficiency (FIG. 2c).

Figure 3:
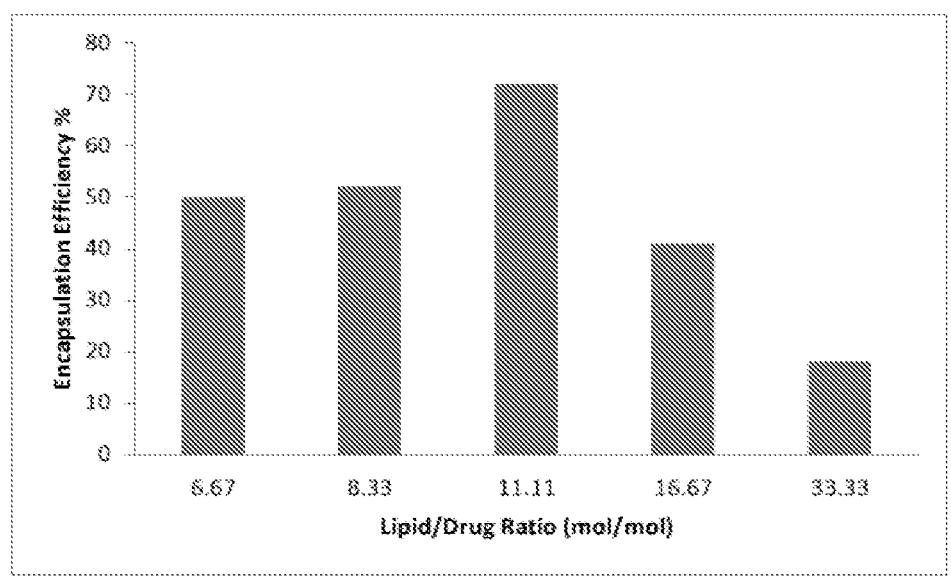
FIG. 3 shows staurosporine encapsulation efficiency according to initial drug to lipid ratio (mole/mole), Staurosporine was loaded into liposomes using the reverse pH gradient method. The bars represent mean encapsulation efficacies calculated from 3 samples, and it can be seen that an optimal drug lipid ratio occurs in terms of encapsulation efficiency at 0.09 (mole/mole).

Optimal Lipid to Drug Ratio for Efficient Encapsulation:

In order to determine how escalating drug concentrations would affect loading efficiency and/or formulation stability, staurosporine was added in lipi-to-drug ratios of 33.33, 16.67, 11.11, 8.33, or 6.67 (mole/mole) Staurosporine uptake into the liposomes was measured as described in the methods, and as shown in FIG. 3 an optimal lipid to drug ratio was obtained. Liposomal loading capacity was highest when lipid to drug ratio was 11.11 (mole/mole), with a peak value of 70% which is higher than for previously described formulations (Yamauchi, M. et al., *Int J Pharm* 2008, 351 (1-2), 250-8).

Figure 4A:
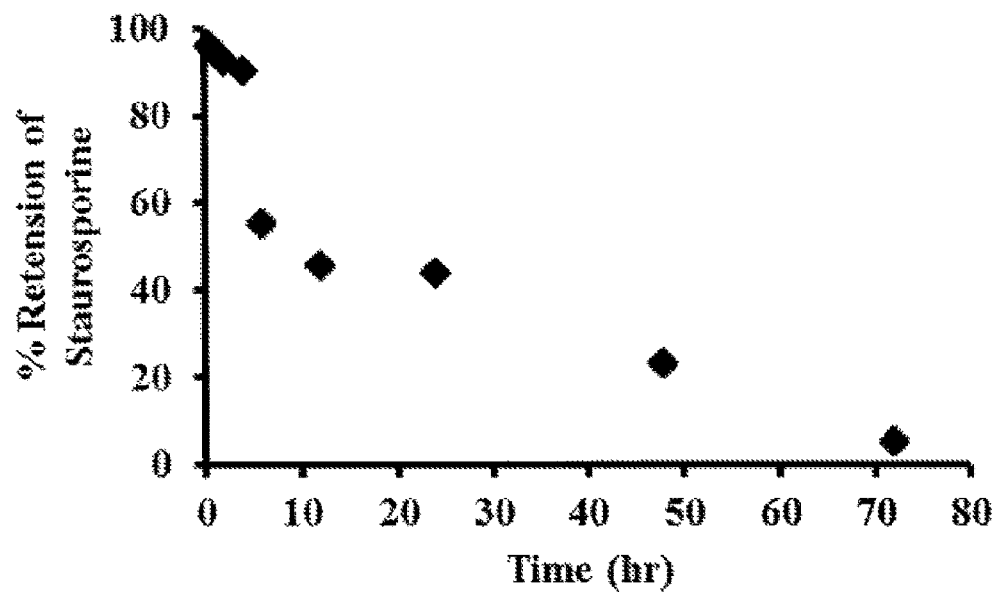
FIGS. 4A-B demonstrate staurosporine was retained within liposomes incubated in vitro with (FIG. 4A) PBS and (FIG. 4 B) human serum. Retention was measured after incubation in serum at room temperature for a range of times. Staurosporine liposomes were separated from the incubation medium by column chromatography, the staurosporine measured spectrophotometrically for liposomes incubated in PBS and with HPLC for those incubated in serum. Virtually all the staurosporine was contained within the liposomes at 3 hours of incubation in PBS or serum, with approximately 80% of the staurosporine remaining after 6 hours of incubation.
Figure 4B:
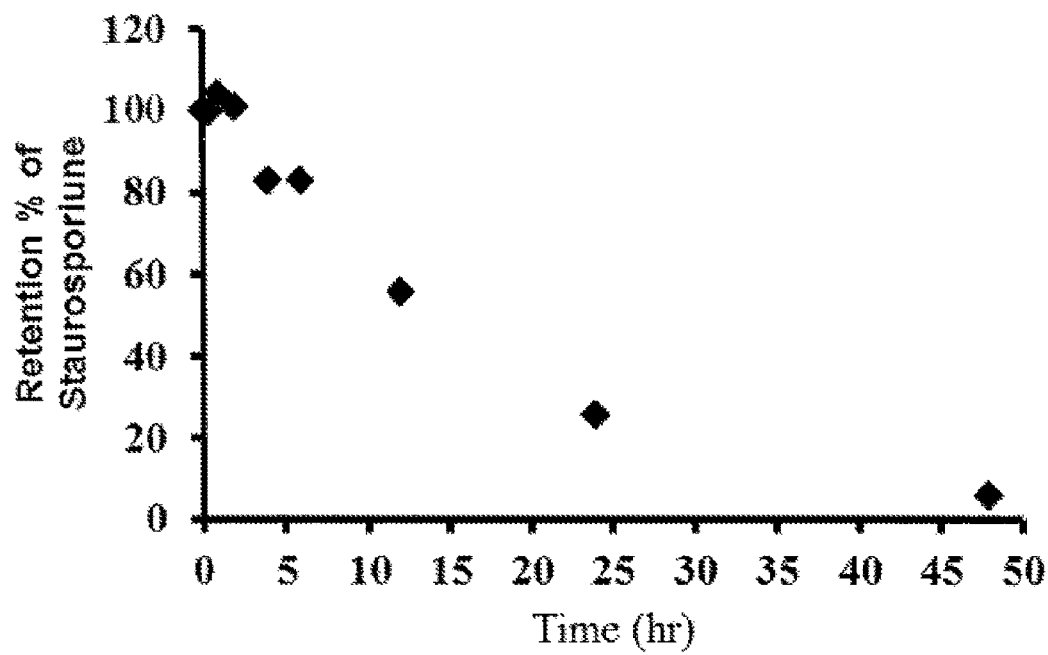
Figure 5A:
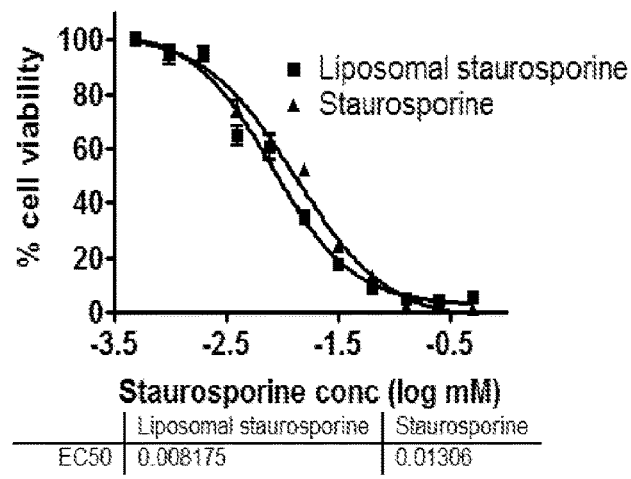
FIGS. 5A-F show in vitro cytotoxicity of liposomally encapsulated staurosporine. The MTT Cell viability assay of staurosporine liposomes and free staurosporine was performed with human glioblastoma cell lines, both established and freshly derived from surgical isolates. The experiments were carried out in triplicate with data represented as the mean±SEM. Each histogram depicts a different cell line.
Figure 5B:
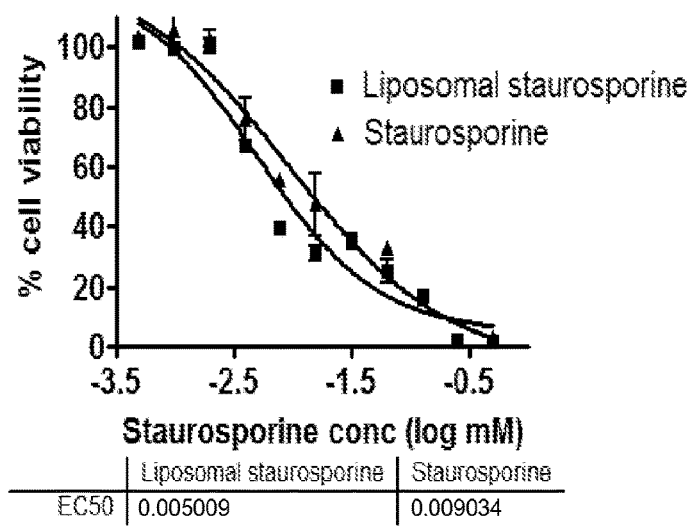
Figure 5C:
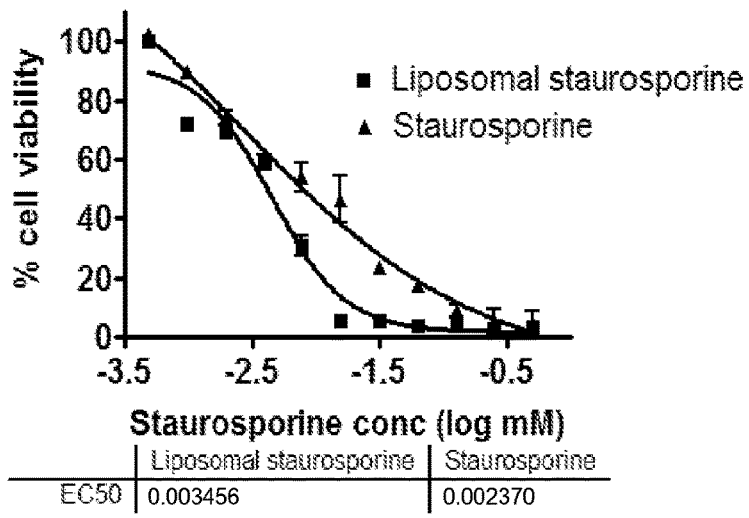
Figure 5D:
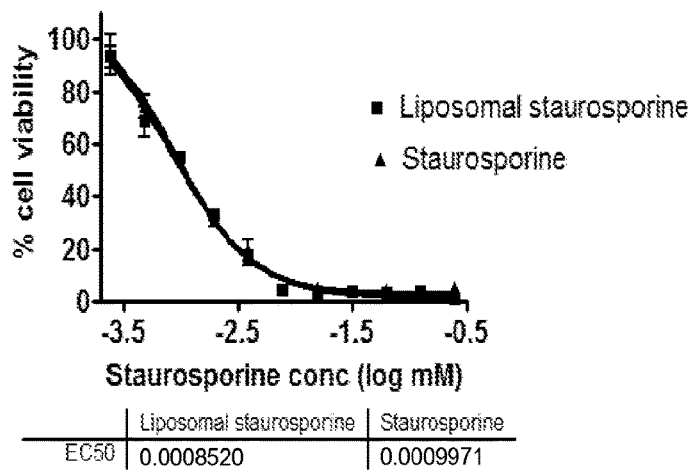
Figure 5E:
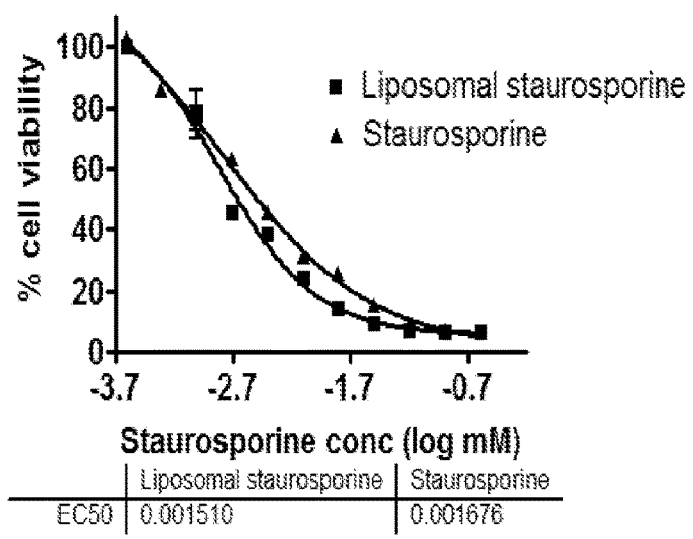
Figure 5F:
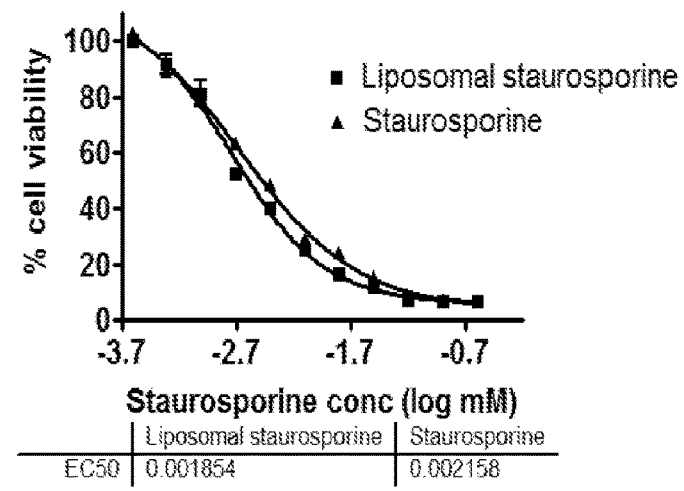

In Vitro Drug Release:

In vitro staurosporine release studies revealed that the encapsulating liposomes were stable for several hours with comparatively little leakage of payload. FIGS. 4a and 4b reveal that after 3 hours of incubation in PBS or human serum, the liposomes retained almost 100% of the initial staurosporine payload. By 4-6 hours of incubation in serum they retained 80% of the staurosporine, and after 12 hours 60% of the compound was still contained. Applicants expect that after 8 hours the PEGylated liposomes will begin to be cleared. The key point is that since liposomal delivery of payload to tumors is efficient due to the enhanced permeability and retention (EPR) effect and also potentially enhanced by targeting, only a low, subtoxic total dose of staurosporine needs to be administered, and thus some leakage of this staurosporine from the liposomes over 24 hours is not expected to be toxic.

Activity of Encapsulated Staurosporine Against Glioblastoma Cell Lines in Vitro:

Encapsulation of staurosporine within liposomes did not impede its cytotoxic effect. Applicants evaluated the inhibitory effect of staurosporine encapsulating liposomes on range of established and freshly derived human glioblastoma cell lines (FIGS. 5a-f). The results depicted in FIGS. 5a-f show that the EC50 of both staurosporine contained in liposomes and free staurosporine was comparable and potent in all cell lines, and ranged from 1-10 nM. This means that encapsulated staurosporine was taken up and released within the tumor cells.

Figure 6A:
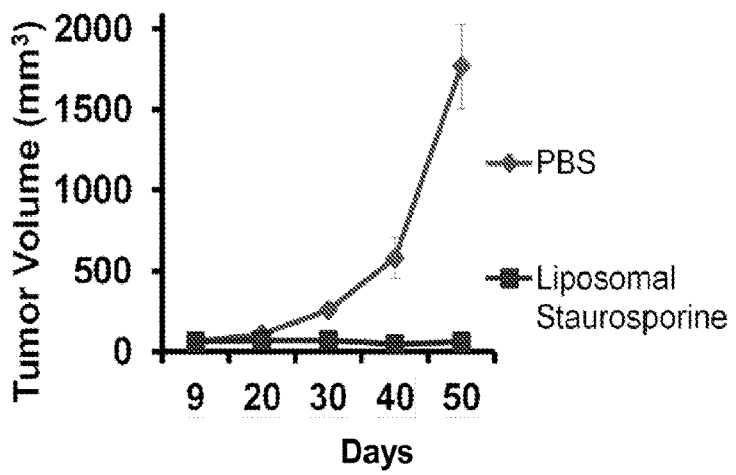
FIGS. 6A-C demonstrate encapsulated staurosporine at a low dose shows in vivo antitumor efficacy with tumor xenograft models.
Figure 6B:
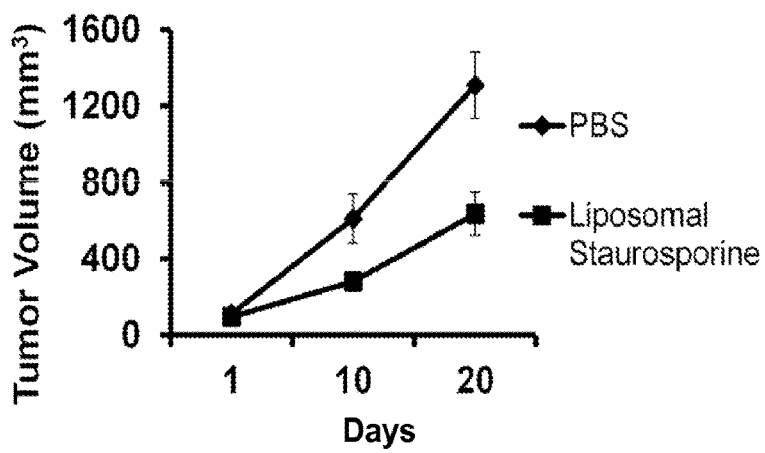
Figure 7:
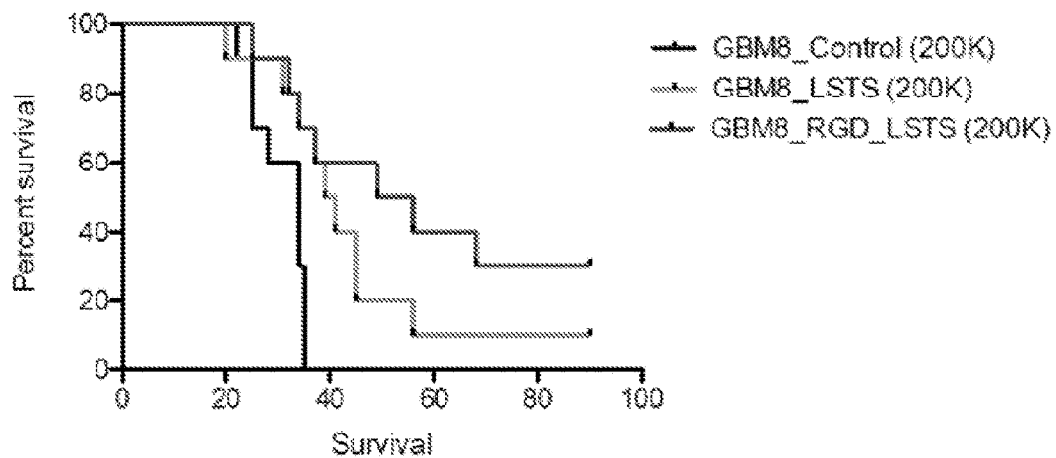
FIG. 7 shows in vivo activity of encapsulated staurosporine, both passively targeted and actively targeted by conjugation to an RGD targeting moiety, in an orthotopic model for brain cancer. The cytotoxic effect of liposomal staurosporine and RGD-liposomal staurosporine on mouse brain cancer cell line GBM8 was evaluated. The results show that both passive and active targeted treatments in mice provided significantly improved survival compared to control mice.
Figure 8A:
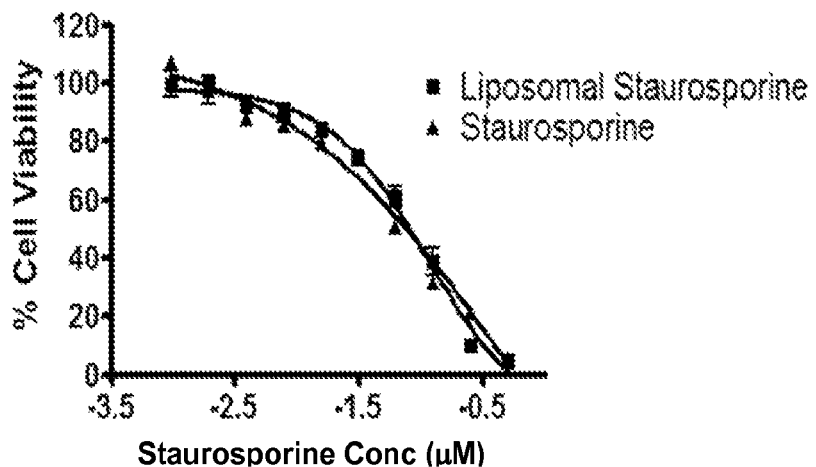
FIGS. 8A-C show in vitro activity of encapsulated staurosporine against a broad range of human cancer cell lines. The cytotoxic effect of liposomal staurosporine and free staurosporine on established human cancer cell lines PC3 pancreatic (FIG. 8B) and MDAMB231 (FIG. 8A) breast cancer cells and mouse melanoma cell line B16F10 (FIG. 8C) was evaluated. The results show that the EC50 of both liposomal and free staurosporine were between 10-50 UM (FIGS. 8A-8C).
Figure 8B:
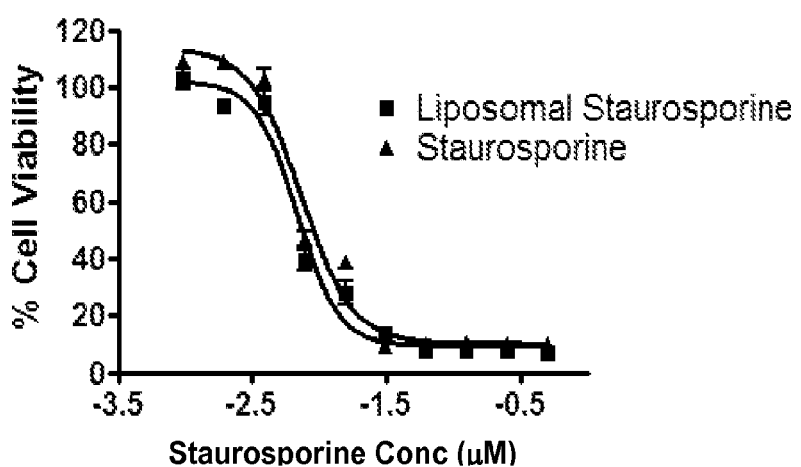
Figure 8C:
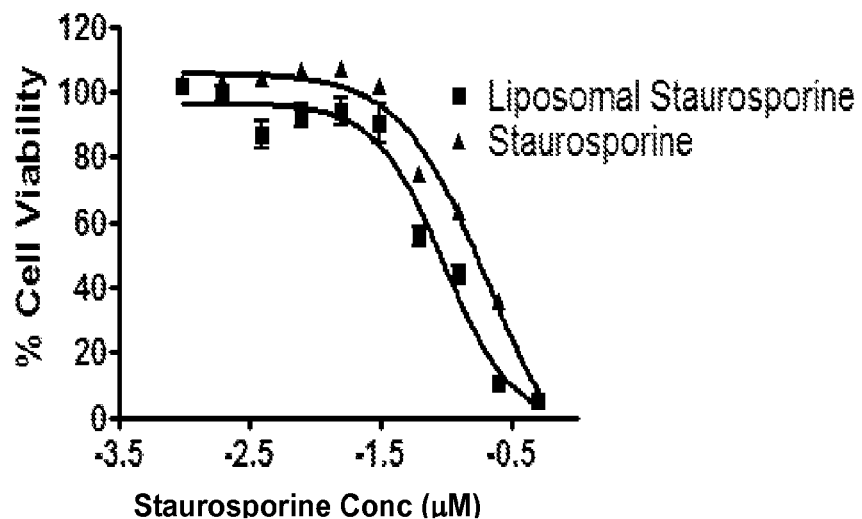
Figure 9A:
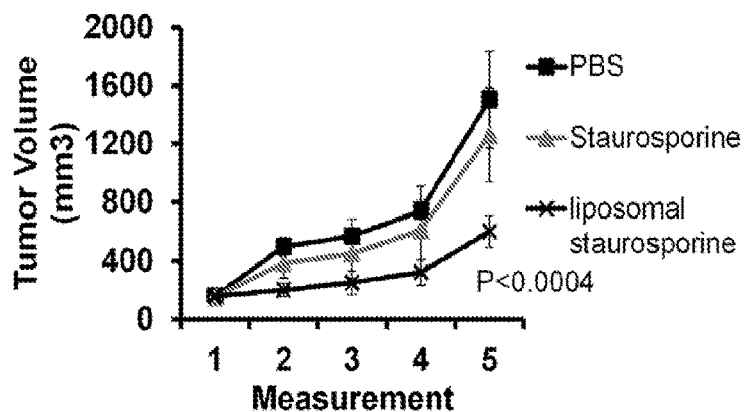
FIGS. 9A-D show in vivo anti-tumor activity of encapsulated staurosporine. Athymic nu/nu mice (5-6 weeks old) were subcutaneously inoculated in the right and left flanks with 2 million U87 cells. The tumors were allowed to grow very large 180-200 mm³ before treatment was started, treatment with liposomal staurosporine over two weeks markedly slowed the growth of the tumors relative to those treated by PBS and free staurosporine (FIGS. 9A and 9B). The photographs in FIG. 9B show a very consistent size reduction in treated tumors with very little variance, indicating a real, substantial, and statistically significant effect (p<0.004), and revealing that free staurosporine had no demonstrable effect. However, free staurosporine was toxic, as body weight did decline, while liposomal staurosporine and PBS-treated animals had no weight difference (FIG. 9C). Ki-67 staining in tumor revealed that tumor proliferation was significantly reduced with liposomal staurosporine treatment (p<0.03.
Figure 9B:
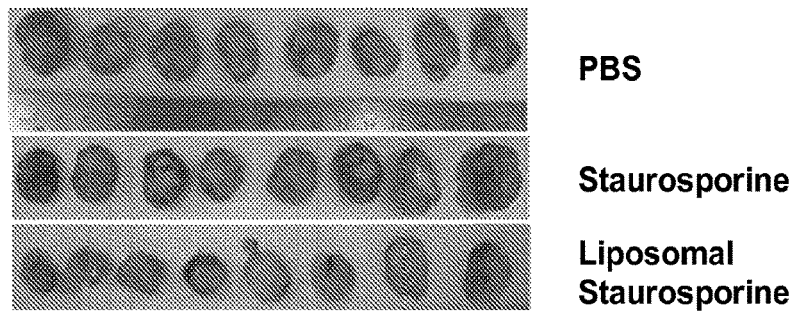
Figure 9C:
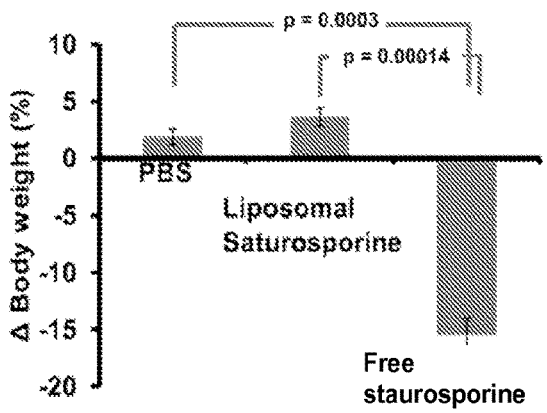
Figure 9D:
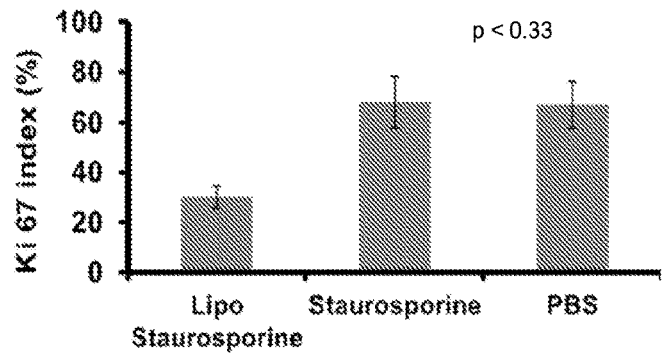

Encapsulated Staurosporine Exhibits In Vivo Anti-Tumor Activity with No Overt Evidence of Toxicity:

Applicants then addressed the essential question of whether a sub-toxic dose of staurosporine encapsulated in liposomes could remain in the blood circulation long enough to be delivered to a tumor in vivo causing a significant anti-tumor effect. If the 0.8 mg/Kg dose Applicants tested were to be injected as free staurosporine, it would very likely be 99% cleared after only one circulatory pass, and after subsequent passes a negligible amount would be present (Gurley L R et al., Staurosporine analysis and its pharmacokinetics in the blood of rats; Los Alamos National Laboratory: Los Alamos, July 1994, 1994). A much higher dose of free staurosporine, 5 mg/Kg, was acutely lethal. Applicants demonstrated that 0.8 mg/kg of staurosporine delivered by non-targeted liposomes completely suppressed tumor growth in the flank model for 50 days after the tumors were already well established (FIG. 6a). Moreover as shown in FIG. 6b the mice treated with 0.8 mg/kg of encapsulated staurosporine or PBS had no statistically significant weight change and exhibited no obvious deleterious effects. In contrast PBS treated mice exhibited rapid growth of their flank tumors. Applicants further demonstrated that 0.8 mg/kg of staurosporine delivered by non-targeted or targeted liposomes significantly improved survival in mice in the GBM8 brain cancer model compared to control mice, as shown in FIG. 7 and Tables 4 and 5, below.

TABLE 4

Comparison of Survival Curves

| | |
|---|---|
| Log-rank (Mantel-Cox) Test Chi square | 9.654 |
| df | 2 |
| P value | 0.0080 |

TABLE 4-continued

Comparison of Survival Curves

| | |
|---|---|
| P value summary | ** |
| Are the survival curves significantly different? | Yes |
| Log-rank test for trend Chi square | 8.300 |
| df | 1 |
| P value | 0.0040 |
| P value summary | ** |
| Sig. trend? | Yes |

TABLE 5

| | GBM8_Control (200K) | GBM8_LSTS (200K) | GBM8_RGD_LSTS (200K) |
|---|---|---|---|
| Number of rows | 40 | 40 | 40 |
| # of blank lines | 30 | 30 | 30 |
| # rows with impossible data | 0 | 0 | 0 |
| # censored subjects | 0 | 1 | 3 |
| # deaths/events | 10 | 9 | 7 |
| Median survival | 34 | 40 | 52.5 |

Figure 6C:
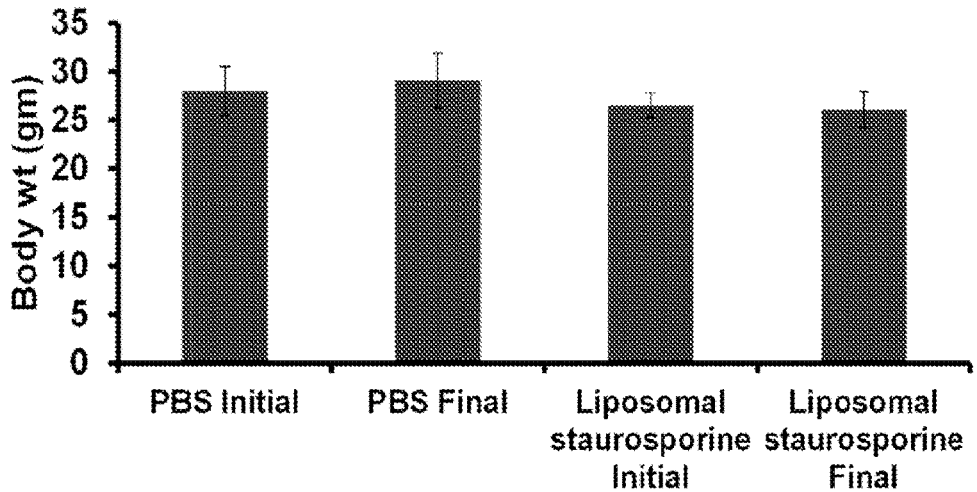

When treatment was stopped and the staurosporine treated mice experienced tumor regrowth during the ensuing 5 weeks, they were separated into two groups and treated with either PBS or liposomal staurosporine for one week, and then the animals were only observed for the next two weeks. It can be seen from FIG. 6c that three treatments with liposomal staurosporine significantly slowed the growth of the tumors, which had become very large, relative to PBS treatment.

The objective of this study was to efficiently load staurosporine into liposomes so that a low dose could be systemically administered while at the same time selectively concentrated at a tumor to attain a therapeutic local dose. Staurosporine is a potent anti-tumor agent but at relatively non-toxic systemic dose levels it is almost entirely removed from the circulation in one complete circuit of the blood, while higher doses have significant toxicity due to the non-selectivity of this pan kinase inhibitor (Gurley L R et al., Staurosporine analysis and its pharmacokinetics in the blood of rats; Los Alamos National Laboratory: Los Alamos, July 1994, 1994). These Obstacles can potentially be overcome by loading staurosporine into liposomes to (1) shield it from protein binding and prevent clearance, and (2) selectively deliver it to tumors via leaky tumor vasculature, a well-documented process termed the enhanced permeability and retention (EPR) effect (Wang, A. Z. et al., Nanoparticle Delivery of Cancer Drugs. *Annu Rev Med* 2011).

Liposomal loading based on chemical gradients to drive the accumulation of a drug payload represents a key advance in terms of efficiency and simplicity (Madden, T. D. et al., *Chem Phys Lipids* 1990, 53 (1), 37-46; Stensrud, G. et al., *Int J Pharm* 2000, 198 (2), 213-28) This gradient-based approach was considerably advanced by the concept of using ammonium ion liposomal transmembrane gradients to form a self-sustaining pH gradient (Haran, G. et al., *Biochim Biophys Acta* 1993, 1 151 (2), 201-15). Attempted gradient based loading of liposomes with staurosporine has yielded poor results, but gradient methods are quite desirable in terms of overall efficiency, so in the present study Applicants focused on the strategy of adapting gradient methodology (Yamauchi, M. et al., *Biol Pharm Bull* 2005, 28 (7), 1259-64). Applicants initially examined the role of external versus internal pH and found that that a reversal of the typically used pH gradient dramatically increased staurosporine loading efficiency. An internal versus external buffer pH of 7.4 and 3, respectively, was effective at driving staurosporine into liposomes. Applicants next explored the effects of various buffers, and the drug to lipid ratio. HEPES and PBS external buffers had equal effect, while internal buffers based on ammonium salts were associated with much higher staurosporine loading than were sodium salts, with the best results acquired using ammonium phosphate. Furthermore, Applicants found an optimal drug (staurosporine) to lipid ratio in terms of the efficiency of liposomal staurosporine loading.

Applicants' reverse loading methodology also offered an advantage in terms of liposomal staurosporine retention. Prevention of premature release of drug payload by circulating liposomes is an essential requirement, but payload release still has to occur at the tumor site. Previous gradient loading methods only supported the liposomal retention of weakly basic anthracyclines such as doxorubicin and to some extent the campothecin analogues (Madden, T. D. et al., *Chem Phys Lipids* 1990, 53 (1), 37-46; Stensrud, G. et al., *Int J Pharm* 2000, 198 (2), 213-28). Other drug chemotypes such as cationic compounds could not be retained. The reverse pH gradient loading methodology Applicants describe resulted in stable liposomal staurosporine encapsulation with essentially all compounds still contained after 3 hours of incubation in human serum. As a result the liposomal outer shell did not have to be modified by extensive cross-ng and the addition of stabilizers to slow payload efflux. Despite stable liposomal retention the release of staurosporine at the tumor site appeared to take place, as evidenced by the significant anti-tumor effect Applicants observed in the glioblastoma flank tumor model.

An important demonstration in this study was that staurosporine could be efficiently loaded into liposomes. Furthermore, Applicants obtained evidence of antitumor activity at a low apparently non-toxic systemic dose, showing that the compound was not cleared before tumor accumulation and a significant anti-tumor effect developed. The present report is intended to provide the basis for later, more comprehensive studies on the efficacy and toxicology of low dose encapsulated staurosporine as a potential glioblastoma therapeutic. In addition, the use of reverse gradient loading for liposomal encapsulation may be applicable to other drug chemotypes.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter, which are obvious to those skilled in chemistry, biochemistry, or related fields are intended to be within the scope of the following claims.

We claim:

1. A liposome composition comprising:
    a plurality of lipid moieties, wherein said lipid moieties form an interior cavity within said liposome; and
    a therapeutic drug encapsulated within said interior cavity, wherein said interior cavity further comprises an interior cavity aqueous medium;
    wherein the therapeutic drug is staurosporine, a pharmaceutically acceptable salt of staurosporine, a staurosporine analogue, or a pharmaceutically acceptable salt of a staurosporine analogue;
    wherein said therapeutic drug is present at a lipid:drug weight ratio of at up to 15:1 w/w; and wherein said interior cavity aqueous medium has a pH of about 7 to about 8.

2. The liposome composition of claim 1, wherein said therapeutic drug is staurosporine or a pharmaceutically acceptable salt of staurosporine.

3. The liposome composition of claim 1, wherein the pharmaceutically acceptable salt is phosphate or sulfate.

4. The liposome composition of claim 1, wherein said interior cavity aqueous medium has a pH of about 7.4 to about 7.6.

5. The liposome composition of claim 1, wherein said liposome has a diameter of about 20 nm to about 10 μm.

6. The liposome composition of claim 1, wherein said therapeutic drug is loaded into said liposome at a loading efficiency of at least 90%.

7. The liposome composition of claim 1, wherein said liposome composition further comprises a targeting moiety conjugated to a portion of said plurality of lipids.

8. The liposome composition of claim 7, wherein said targeting moiety is an Arginine-Glycine-Aspartate (RGD)-targeting moiety.

9. The liposome composition of claim 1, wherein the staurosporine analogue is 7-hydroxystaurosporine; bisindolylmaleimide; or benzoylstaurosporine.

10. The liposome composition of claim 1, wherein the therapeutic drug is present at a lipid:drug weight ratio of at up to 10:1 w/w.

11. The liposome composition of claim 1, wherein the lipid moieties comprise a phospholipid, a cholesterol, or a combination thereof.

12. The liposome composition of claim 11, wherein the phospholipid comprises phosphatidylcholine, phosphatidic acid, phosphatidylethanolamine, phosphatidylglycerol, phosphatidylserine, and phosphatidy linos itol, dimyristoyl-phosphatidylcholine, distearoylphosphatidylcholine, dioleoylphosphatidylcholine, dipalmitoylphosphatidylcholine, dimyristoylphosphatidylglycerol, distearoylphosphatidyl-glycerol, dioleoylphosphatidylglycerol, dipalmitoylphosphatidylglycerol, dimydstoylphosphatidylserine, distearoylphosphatidylserine, dioleoylphosphatidylserine, dipalmitoylphosphatidylserine, dioleoyl phosphatidylethanolamine, palmitoyloleoylphosphatidylcholine, palmitoyloleoyl-phosphatidylethanolamine, dioleoylphosphatidylethanolamine 4-(N-maleimidomethyl)-cyclohexane-1-carboxylate, dipalmitoylphosphatidylethanolamine, dimyristoylphosphoethanolamine, distearoylphosphatidylethanolamine, 16-O-monomethyl-phosphatidylethanolamine, 16-O-dimethyl-phosphatidylethanolamine, 18-1-trans-phosphatidylethanolamine, 1-stearoyl-2-oleoyl-phosphatidy ethanol amine, 1,2-dielaidoyl-sn-glycero-3-phophoethanolamine, cardiolipin, or a combination of two or more thereof.

13. The liposome composition of claim 11, wherein the phospholipid comprises dioleoylphosphatidylethanolamine, distearoylphosphatidylcholine, and distearoylphosphatidylethanolamine.

14. A method of treating brain cancer in a subject in need thereof, said method comprising administering to said subject a therapeutically effective amount of the liposome composition of claim 1.

\* \* \* \* \*

SEQUENCE LISTING

<160> NUMBER OF SEQ ID NOS: 21

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Cys Arg Gly Asp Lys Gly Pro Asp Cys
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 2

Arg Lys Xaa Xaa Arg Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Cys Val Asn His Pro Ala Phe Ala Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Lys Leu Ala Lys Leu Ala Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Cys Asp Cys Arg Gly Asp Cys Phe Cys
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

```
<400> SEQUENCE: 6

Cys Asn Gly Arg Cys Val Ser Gly Cys Ala Gly Arg Cys
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Cys Asn Gly Arg Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Cys Thr Pro Ser Pro Phe Ser His Cys
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ile Phe Leu Leu Trp Gln Arg
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Cys Thr Thr His Trp Gly Phe Thr Leu Cys
1               5                   10

<210> SEQ ID NO 11
<211> LENGTH: 31
<212> TYPE: PRT
<213> ORGANISM: Artificial Sequence
<220> FEATURE:
<223> OTHER INFORMATION: Synthetic peptide

<400> SEQUENCE: 11

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 12
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 12

Cys Ser Arg Pro Arg Arg Ser Glu Cys
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Cys Gly Lys Arg Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Cys Asp Thr Arg Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Cys Lys Ala Ala Lys Asn Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Cys Lys Gly Ala Lys Ala Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Cys Arg Gly Arg Arg Ser Thr
1               5

<210> SEQ ID NO 18
<211> LENGTH: 11
<212> TYPE: PRT
<213> ORGANISM: Artificial Sequence
```

```
<220> FEATURE:
<223> OTHER INFORMATION: Synthetic peptide

<400> SEQUENCE: 18

Cys Arg Gly Asp Lys Arg Gly Pro Asp Glu Cys
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Cys Pro Arg Glu Cys Glu Ser Ile Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Cys Gly Asn Ser Asn Pro Lys Ser Cys
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21

Ser Val Ser Val Gly Met Lys Pro Ser Pro Arg Pro
1               5                   10
```